(12) United States Patent
Luthra et al.

(10) Patent No.: US 7,655,038 B2
(45) Date of Patent: Feb. 2, 2010

(54) POLYMERIC NETWORK SYSTEM FOR MEDICAL DEVICES AND METHODS OF USE

(75) Inventors: Ajay K. Luthra, Ruislip (GB); Shivpal S. Sandhu, Slough (GB)

(73) Assignee: BioInteractions Ltd., Reading, Berkshire (GB)

( * ) Notice: Subject to any disclaimer, the term of this patent is extended or adjusted under 35 U.S.C. 154(b) by 780 days.

(21) Appl. No.: 10/790,338

(22) Filed: Mar. 1, 2004

(65) Prior Publication Data
US 2004/0170752 A1    Sep. 2, 2004

Related U.S. Application Data

(60) Provisional application No. 60/451,333, filed on Feb. 28, 2003.

(51) Int. Cl.
| | |
|---|---|
| *A61F 2/06* | (2006.01) |
| *B32B 7/02* | (2006.01) |
| *B32B 27/08* | (2006.01) |
| *C08F 120/06* | (2006.01) |

(52) U.S. Cl. ............... 623/1.42; 623/1.46; 428/213; 428/520; 526/317.1; 526/318; 526/319

(58) Field of Classification Search ............ 428/213, 428/520; 526/317.1, 318, 319; 623/1.42, 623/1.46
See application file for complete search history.

(56) References Cited

U.S. PATENT DOCUMENTS

| | | | |
|---|---|---|---|
| 5,464,650 A | 11/1995 | Berg et al. | |
| 5,637,113 A * | 6/1997 | Tartaglia et al. | 623/1.42 |
| 5,782,908 A | 7/1998 | Cahalan et al. | |
| 5,843,089 A * | 12/1998 | Sahatjian et al. | 623/1.11 |
| 5,900,246 A | 5/1999 | Lambert | |
| 5,980,972 A | 11/1999 | Ding | |
| 6,214,901 B1 | 4/2001 | Chudzik et al. | |
| 6,224,625 B1 * | 5/2001 | Jayaraman | 623/1.15 |
| 6,231,600 B1 | 5/2001 | Zhong | |
| 6,251,136 B1 | 6/2001 | Guruwaiya et al. | |
| 6,287,379 B1 | 9/2001 | Khalifeh | |
| 6,387,379 B1 | 5/2002 | Goldberg et al. | |
| 6,503,556 B2 | 1/2003 | Harish et al. | |
| 6,517,858 B1 | 2/2003 | Le Moel et al. | |
| 6,530,950 B1 * | 3/2003 | Alvarado et al. | 623/1.13 |
| 6,653,426 B2 | 11/2003 | Alvarado et al. | |
| 6,673,385 B1 | 1/2004 | Ding et al. | |

(Continued)

FOREIGN PATENT DOCUMENTS

EP    0425200    5/1991

(Continued)

*Primary Examiner*—Kevin R. Kruer
(74) *Attorney, Agent, or Firm*—Dardi & Herbert, PLLC

(57) ABSTRACT

Methods of making a coating on a medical device are disclosed, including associating a composition with at least a portion of the device to form a layer. In some embodiments, a composition may include a copolymer prepared from a room temperature melt of a plurality of monomer units that comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit.

113 Claims, 8 Drawing Sheets

U.S. PATENT DOCUMENTS

| | | |
|---|---|---|
| 2002/0002353 A1 | 1/2002 | Michael et al. |
| 2002/0133183 A1* | 9/2002 | Lentz et al. ............... 606/155 |
| 2002/0150549 A1 | 10/2002 | Vogt et al. |
| 2002/1937475 | 12/2002 | Hossainy et al. |
| 2004/0142016 A1* | 7/2004 | Luthra et al. ............... 424/423 |

FOREIGN PATENT DOCUMENTS

| | | |
|---|---|---|
| EP | 09/50386 | 10/1999 |
| WO | WO 00/41687 | 7/2000 |
| WO | WO 00/41738 | 7/2000 |
| WO | WO 01/01890 | 1/2001 |
| WO | WO 01/87342 | 11/2001 |
| WO | WO 03/024500 | 3/2003 |
| WO | WO 2004/009145 | 1/2004 |

* cited by examiner ced below about 2500, wherein the copolymer comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit. Such methods may be optionally performed with the monomer units being polymerized to form the copolymer after the monomer units have been associated with the medical device.

POLYMERIC NETWORK SYSTEM FOR MEDICAL DEVICES AND METHODS OF USE

CROSS REFERENCE TO RELATED APPLICATIONS

The present application claims the benefit to U.S. Provisional Patent Application Ser. No. 60/451,333, filed Feb. 28, 2003, which is hereby incorporated by reference.

Other copending applications that are commonly owned and assigned, and may be related with respect to some subject matter, are U.S. patent applications Ser. Nos. 10/179,453, filed Jun. 26, 2002, and 10/750,706, filed Jan. 5, 2004, which are hereby incorporated by reference without a claim of priority.

FIELD OF THE INVENTION

The inventions are, in general, related to the field of coatings for medical devices, and certain embodiments relate to drug delivery using the same.

BACKGROUND

Coated medical devices, such as stents, catheters, guide wires, vascular grafts and the like, are frequently used in numerous medical procedures. The utility of these devices may be enhanced by therapeutic, diagnostic, lubricious or other materials coated onto the device which can be delivered, or released, from the device to a specific site within the patient. With the number of medical procedures utilizing medical devices such as stents and catheters, it would be desirable to provide coated medical devices that release therapeutic or diagnostic agents within a patient in a controlled manner.

A conventional technique for introducing a drug into a medical device coating is to apply the coating to the device, swell the coating in a solvent in the presence of a drug that is dissolved in the solvent, and to remove the solvent. The swelling of the coating allows the drug to interpenetrate the coating, where it remains after the solvent is removed.

SUMMARY OF THE INVENTION

Set forth herein are techniques that include loading a drug into a copolymer before the copolymer-drug combination is coated onto a device. This process is advantageous because the copolymer drug may be deposited in a layer or series of layers to form a coating on the medical device. Coatings intimately contact the device for improved adherence and other properties helpful when the device is implanted. Further, coatings are more conveniently adapted to production processes than alternative processes such as molding a sheath or packing a sheath around the device.

An embodiment is a method of making a coating on a medical device for delivery of a therapeutic agent. For example, this method may be done by associating a composition with at least a portion of the device to form a first layer, wherein the composition comprises the therapeutic agent associated with a copolymer that optionally has a molecular weight of at least about 2500, wherein the copolymer comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit. Such methods may be optionally performed with the monomer units being polymerized to form the copolymer after the monomer units have been associated with the medical device.

Another embodiment is a coating for a medical device for delivery of a therapeutic agent. The coating may include a layer having a composition associated with at least a portion of the device, wherein the composition comprises the therapeutic agent associated with a copolymer that optionally has a molecular weight of at least about 2500, wherein the copolymer comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit. Coatings formed by such methods may optionally include a second layer that contacts at least a portion of the first layer, wherein the second layer and the first layer have a different composition.

Another embodiment is a method of making a coating on a medical device by associating a composition with at least a portion of the device to form a layer, wherein the composition comprises a copolymer that optionally has a molecular weight of at least about 2500, wherein the copolymer is prepared from a room temperature melt of a plurality of monomer units that comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit. Such methods may be optionally be performed with the monomer units being polymerized to form the copolymer after the monomer units have been associated with the medical device.

DETAILED DESCRIPTION

Figure 1A:
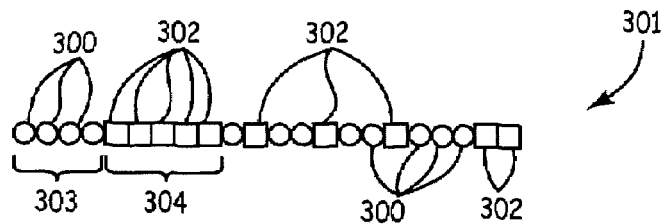
FIG. 1 depicts in Frame (A) an illustration of domains formed by blocks in copolymers, and possible mechanisms in Frames (B), (C) and (D) of therapeutic drug association or entrapment

Copolymers are described that form associations with therapeutic agents so that the copolymer-agent complex may be used in subsequent processing steps, e.g., forming a layer on a medical device. Without being limited to a particular theory, the advantageous properties presented by the copolymer domains may be the result of primary, secondary and/or tertiary structure of the resulting macromolecules. The domains may be created by the association of blocks on the copolymers, as shown in FIG. 1A. In particular, therapeutic agents may become trapped in microcavities formed by the copolymers. The domains possibly form because of thermodynamic forces and chemical associations between the blocks force the blocks to associate. This phenomenon may advantageously be exploited to make materials with enhanced properties for carrying and releasing therapeutic agents.

Embodiments herein include, for example, copolymers having blocks that have different glass transition temperatures (Tgs). Blocks with significantly different glass transition temperatures typically have the chemical properties that result in the creation of domains. Further, association of a therapeutic agent with the blocks may be accomplished with Tgs that are at least about 30, 50, or 70° Celsius (C.) different, or within subranges of these specific ranges. Moreover, the combination of blocks may be made to have an average Tg that is comparable to a physiological temperature of a patient that receives an implant that has such a copolymer. Thus, a copolymer may, in addition to one or more of the other features already described, be made to be with a composition of monomeric units that have an average Tg that approaches a physiological temperature of about 37° C. Calculation and determination of Tg is discussed in more detail, below.

Without being bound to a particular theory, the formation of blocks may contribute to some of the properties of polymers described herein. Referring to FIG. 1A, a copolymer 301 is depicted with monomeric units 300 and having a Tg that is relatively low compared to higher Tg monomeric units 302. The monomeric units are reacted to form copolymers that may include blocks. Low Tg monomeric units 300 and high Tg monomeric units 302 may tend to form domains 303 and 304, respectively. As discussed below, describing monomeric units as having a Tg that is equal to the Tg of the homopolymer formed by such a monomeric unit provides some useful approximations for properties of copolymers 301 and domains such as 303, 304. Referring to a domain such as 303, 304 as having a Tg that is equal to the Tg of the homopolymer formed by such a monomeric unit also provides some useful insights. In a general perspective, glass transition temperature (Tg) of a polymer depends on chain geometry, chain flexibility and molecular aggregates. Domains in a polymer have an influence in Tgs since domains will impact on chain geometry, chain flexibility and molecular aggregates.

Figure 1B:
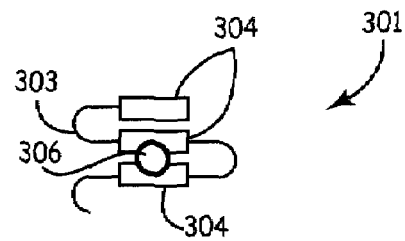

FIG. 1B shows a single copolymer 301 with low Tg domains 303 and high Tg domains 304, with the high Tg domains 304 being more ordered, particularly at a temperature below Tg for the high Tg domains 304 and above the low Tg domains 303. Therapeutic agent 306 forms an association with domains 304. Such associations may be driven by, e.g., ionic, polar, or hydrophobic-hydrophilic interactions. As the ambient temperature is increased to approach the Tg of monomeric units 302, the domains 304 are expected to have more mobility and to release therapeutic agent 306 more readily.

Figure 1C:
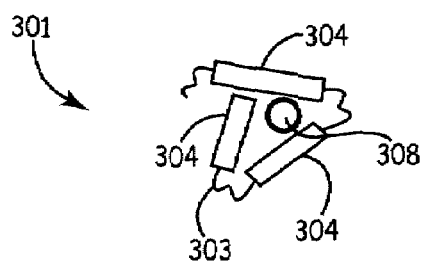

FIG. 1C shows copolymer 301 with low Tg domains 303 and high Tg domains 304. The conformation of copolymer 301 entraps therapeutic agent 308. Such a conformation might be achieved in a liquid or in a solid, e.g., a polymeric layer. A liquid may include, e.g., a melt or a composition containing water or an organic solvent.

Figure 1D:
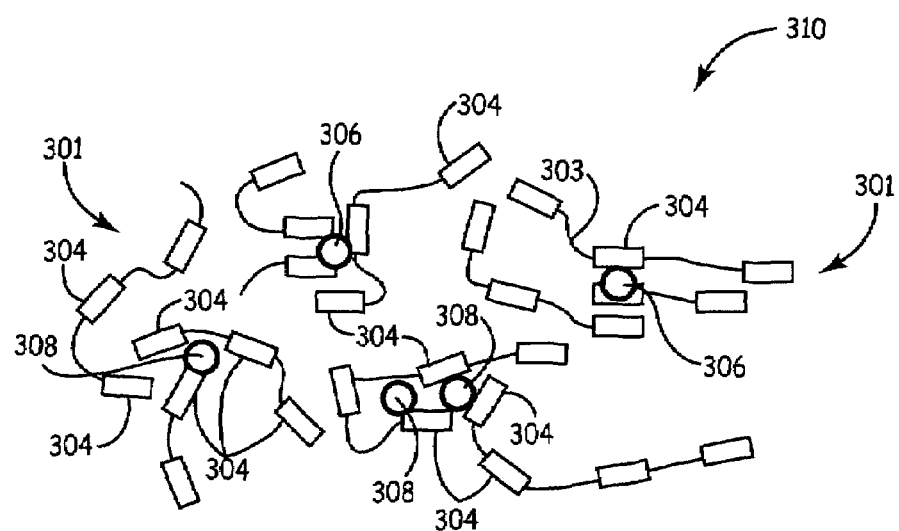

FIG. 1D shows a composition 310 comprising multiple copolymers 301. Such a composition could be, for instance, a liquid or a solid, e.g., a layer. Domains 304 tend to form associations with each other that allow for binding events or other associations to occur between domains 304 and therapeutic agent 306. Alternatively, domains 304 may form conformations that have microcavities containing therapeutic agent 308. Such microcavities might form as a result of the domains associating with, and packings around therapeutic agents 308. Alternatively, a stiffness of domains 304 may create packing inefficiencies that are microcavities that may subsequently be occupied by therapeutic agent 308.

Glass Transition Temperature and Polymer Terminology

Certain embodiments of copolymers described herein are related to the property referred to as Tg. Tg is the temperature at which an amorphous polymer (or the amorphous regions in a partially crystalline polymer) changes from a hard and relatively brittle condition to a viscous or rubbery condition. Glass transition temperatures may be measured by methods such as differential scanning calorimetery (DSC) or differential thermal analysis. Other methodologies include volume expansion coefficient, NMR spectroscopy and refractive index. Tg is a property of a polymer.

Figure 2:
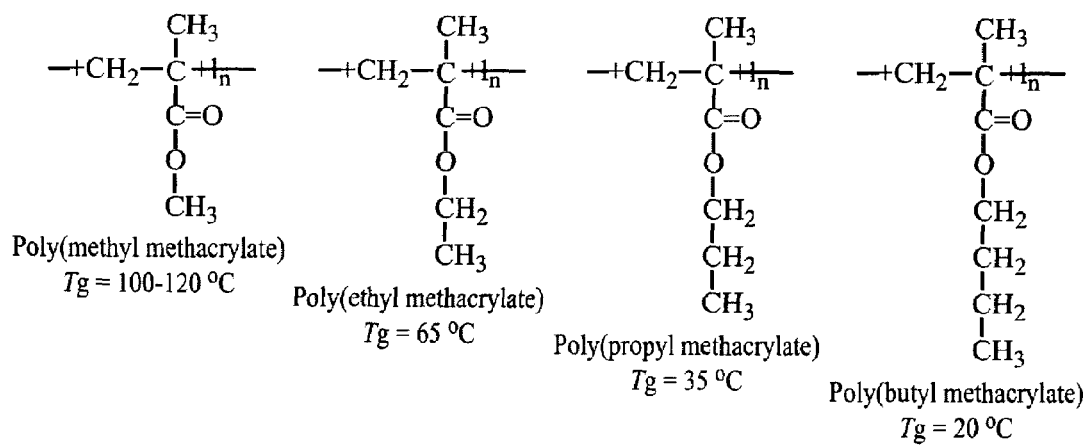
FIG. 2 shows examples of monomeric units, and also indicates the Tg of homopolymers formed from such units.

A polymer is a molecule composed of repeated subunits. Each subunit is referred to herein as a monomeric unit. Polymers of only a few monomeric units are sometimes referred to as oligomers. A monomeric unit may be the reaction product of a reactive monomer, but is not limited to that meaning. Reactive monomers are reacted to form polymers of monomeric units. The term polymer includes the meanings of homopolymer, copolymer, terpolymer, block copolymer, random copolymer, and oligomer. FIG. 2 shows examples of monomeric units, and also indicates the Tg of homopolymers formed from such units. Tgs for other homopolymers are: polybutylacrylate −49° C., poly(tert-butyl methacrylate 107° C., poly(butyl methacrylate-co-isobutyl methacrylate) 35° C., poly(butyl methacrylate-co-methyl methacrylate) 64° C., polyethyl acrylate −23° C., poly(2-ethylhexyl acrylate) −55° C., and poly(2-ethylhexyl methacrylate) −10° C. The Tgs for homopolymers are known to persons of ordinary skill in these arts and are readily available from public sources, e.g., from the ALDRICH catalog, polymer encyclopaedias, and the Polysciences Inc Polymer & Monomer Catalog. And, for example, the U.S. Pat. No. 6,653,426 provides other details.

Some embodiments herein are directed to copolymers having certain Tg values or averages. Unless otherwise specified, the average Tg values are to be calculated on the basis of weight of the monomer units. An alternative method is to calculate an average by molar weight. The Tg for a homopolymer varies with MW until about 20,000, so that a Tg for a homopolymer is customarily considered its Tg at or above about 20,000 MW. This procedure may be used to calculate the average Tg for a composition of monomeric units that are disposed in a copolymer.

Other aspects of polymers relate to calculating the average polymer weight. One such method is the weight average molecular weight, which is calculated as follows: weigh a number of polymer molecules, add the squares of these weights, and then divide by the total weight of the molecules. The number average molecular weight is another way of determining the molecular weight of a polymer. It is determined by measuring the molecular weight of n polymer molecules, summing the weights, and dividing by n. The number average molecular weight of a polymer can be determined by, e.g., osmometry, end-group titration, and colligative properties.

A polymer may include a block. A series of identical monomeric units joined together forms a block. A polymer may have no blocks, or a plurality of blocks. Blocks from a group of polymers or from one polymer may become associated with each other to form domains. Thermodynamic forces can drive the formation of the domains, with chemical attractions between the blocks contributing to the driving force. For example, some blocks may tend to become associated with each other as a result on ion-ion interactions or hydrophobic-hydrophillic forces. Thus, in some conditions, a composition of polymers having hydrophillic blocks and hydrophobic blocks could be expected to form domains having hydrophobic blocks and domains having hydrophilic blocks. A copolymer is a polymer having at least two different monomeric units. Some copolymers have blocks, while others have random structures, and some copolymers have both blocks and regions of random copolymer bonding. Copolymers may be made from reactive monomers, oligomers, polymers, or other copolymers. Copolymer is a term that encompasses an oligomer made of at least two different monomeric units. Reactive comonomer is a term that may include more than two monomers.

Polymers, Tg, and Copolymers with Monomeric Units having a Predetermined Difference in Tg Certain embodiments herein relate to copolymers formed from monomeric units that form homopolymers that have Tgs that have a selected difference between them. Monomeric units are sometimes referred to herein as having a Tg, by which is meant the Tg of the homopolymer formed of the monomeric unit. Without being bound to a particular theory of operation, the predetermined differences set forth herein are believed to contribute to domain formation so that certain desirable polymeric properties are enhanced. One such property is enhanced association of therapeutic agents with the domains. The domain-domain interactions may create small microvoids for therapeutic agents, or may form chemical associations with the therapeutic agents, which can be bonding associations or electrostatic interactions.

Suitable predetermined Tg differences between monomeric units include at least about 30° C., at least about 50° C., and at least about 70° C. Other suitable differences in monomeric units Tgs are in the range of about 30° C. to about 500° C., about 50° C. to about 300° C., and about 70° C. to about 200° C. Persons of ordinary skill in these arts, after reading this disclosure, will appreciate that all ranges and values within these explicitly stated ranges are contemplated.

Tg is an indirect and approximate indication of mobility of blocks or domains of a composition of copolymers. For copolymers having a non-covalent chemical or physical association with an agent, a greater mobility, or lower Tg, would be expected to result in a faster release of the agent. Other factors that affect release are the size of the agent, its chemical characteristics, and the extent of its association with the polymers around it. Some chemical characteristics are, for example, hydrophilicity, shape/size, presence of charges, and polarity. The most desirable rate of release of an agent, however, is highly dependent on the application. Some situations require a quick release, some require a sustained release, and some require a quick burst, followed by a sustained release. Further, a plurality of agents may be associated with a polymer, or a layer, or a coating, so that the Tgs are adjusted to reflect the chemistries of the agents.

When polymers are deposited in layers, the rate of release from the layer is believed to be at least partially dependent on the size of the domains, with smaller domains releasing agents more quickly than larger domains. Alternatively, it may be that the domains have irregular shapes and orientations that create microcavities. Then, larger domains could pack less efficiently into the layer so as to affect the quality of the microcavities. The microcavities may receive the therapeutic agent, which migrates through the layer to be released. Alternatively, it may be that the domains have irregular shapes and orientations that cause them to fold into three dimensional shapes in a melt or in a solution so as to create microcavities in the folded shape that receive the therapeutic agent. For all of these reasons, it is useful to be able to make polymers, e.g., copolymers, from monomeric units having predetermined differences in Tgs. Further, these considerations point to the advantages of having copolymer systems that can be adjusted to have Tgs within certain ranges.

While recognizing that a significant factor to control agent release is to achieve a particular average Tg for agent-release applications in (or on) a patient's body, the embodiments herein describe a significant advance with respect to control of agent release and elution based on the chemical composition of different monomer units of a copolymer and their corresponding Tgs. This sophisticated use of copolymer design goes far beyond recognition of the significant aspect of agent release from a polymer that can be achieved by choosing polymers having Tgs above or below a certain value.

In addition to choosing a predetermined Tg differences for monomeric units in a copolymer, other embodiments relate to choosing sets of monomeric units with certain Tgs relate to the average Tg of the set. In some embodiments, it is advantageous to choose a particular average Tg. For instance, polymeric implants loaded with a therapeutic agent can be made with polymers or copolymers having a Tg that is close to a physiological temperature. The Tg of the monomeric units in a polymer provides an approximation of the Tg of the resultant polymer. Thus, a weighted Tg average of a composition of monomeric units may be chosen for making a copolymer having desired properties. Alternatively, other applications call for an average Tg that is suitable to achieve a change at a temperature for that application, e.g., movement form cryostorage to superheated steam, from $CO_2$ storage to oven, from freezer to boiling, from a cooler to a hot water bath, and so forth. Weighted Tg averages for copolymers and polymers as set forth herein include from about −200° C. to about 500° C., from about −80° C. to about 250° C., from about −20° C. to about 100° C., from about 0° C. to about 40° C. Persons of ordinary skill in these arts, after reading this disclosure, will appreciate that all ranges and values within these explicitly stated ranges are contemplated.

Persons of ordinary skill in these arts are acquainted with a wide variety of polymers, reactive monomers, and functional groups. Examples of polymers include polyacrylic acid, polyacrlonitrile, polyallyamine, polyacrylates, polybutyl acrylate, polymethylmethacrylate, polyalkyl acrylates, polyalkyl methacrylate, polybutadiene, polycarbomethylsilane, poly (carbonate) urethane; polydimethylsiloxane, polyethylene, polyethylene glycol, polypropylene glycol, poly(ether) urethane, polyurethane, polyvinyl chloride, polyvinyl alcohol, polymaleic anhydride, cellulose nitrate, carboxyl methyl cellulose, dextran, dextran sulphate, polypropylene, polyesters, polycarbonates, polyethers, polybutenes, polymaleic acid, fluoropolymers, unsaturated polymers, polyisoprene, polymelamine, polysulphones, polyureas, biological polymers, proteins, gelatin, collagen, elastin, and copolymers and terpolymers thereof. Monomeric units and reactive monomers associated with these monomeric units are known to persons of skill in these arts.

Examples of monomeric units include butyl acrylate, methyl methacrylate, butyl methacrylate, hydroxyethyl methacrylate, acrylic acid, methacrylate acid, polyethylene glycol, polyethylene glycol monomethacrylate, polyethylene glycol dimethacrylate, polypropylene glycol diglycidal ether, polyethylene glycol diglycidyl ether, isocyanatoethyl methacrylate, N-acryloxysuccinimide, glycidyl methacrylate, hexamethylene diisocyanate, acrolein, crotonaldehyde, glycerol monomethacrylate, heparin methacrylate, methacryloyloxyethyl phosphorylcholine and combinations thereof. Reactive monomers associated with these monomeric units are known to persons of skill in these arts.

In some embodiments, reactive monomers may be bi-functional monomers, while in other embodiments the monomers may be tri-functional or multifunctional monomers. In further embodiments, the reactive monomers comprise a combination of bi-functional, tri-functional and/or multifunctional monomers.

Examples of functional groups include hydroxyl, amine, carboxylic, aldehyde, ketone, thiol, allyl, acrylate, methacrylate, butyl acrylate, isocyanate, epoxide, azides, aziridines, acetals, ketals, alkynes, acyl halides, alky halides, hydroxy aldehydes and ketones, allenes, amides, bisamides, amino acids and esters, amino carbonyl compounds, mercaptans, amino mercaptans, anhydrides, azines, azo compounds, azoxy compounds, boranes, carbamates, carbodimides, carbonates, diazo compounds, isothionates, hydroxamic acid, hydroxy acids, hydroxy amines and amides, hydroxylamine, imines, lactams, nitriles, sulphonamides, sulphones, sulphonic acids and thiocyanates.

Polymers, e.g., copolymers may be made by a variety of processes known to persons of ordinary skill in these arts. Polymers and copolymer may be made from, e.g., reactive monomers, polymers, oligomers, copolymers, and combinations thereof, using various reaction schemes. Examples of reaction schemes include free radical polymerization, addition polymerization, condensation polymerization, electrophile/nucleophile reactions, urethane reactions, and combinations thereof. Reactions that form a polymer may, in some cases, be initiated by an initiator. Examples of polymerization initiators include, for example, thermal initiators, UV initiators, free radical initiators, electromagnetic initiators, polymerization catalysts and combinations thereof. Free radical initiators include, for example, peroxides.

Some embodiments relate to polymers, e.g., copolymers, that have a reactive functional group. Methods of making such polymers include, e.g., using reaction schemes that create the bonds that unite the monomeric units without forming covalent bonds with the reactive functional groups. Another method is to derivatize a polymer after it has been formed by using additional chemical reactions to join a functional group to the polymer. Some schemes are a combination of these methods that involve reacting a functional group on a polymer to add or create a new reactive functional group. Many such reactions are known to persons of ordinary skill in these arts.

Certain embodiments relate to making copolymers from a melt of reactive monomers, or other reactive components. A melt of materials is a composition of those materials that has little or no solvent or diluents, and is a flowable, albeit sometimes highly viscous, liquid. The high concentration of reactable components in the melt may be advantageous in some circumstances, e.g., by helping to form copolymers having a molecular weight that is relatively higher than more dilute compositions. A melt with less than about 5% solvent by volume would be deemed a melt, as that term is used herein. A pure melt is a melt with essentially no solvent or diluents.

Some embodiments relate to polymers, e.g., copolymers, having a certain molecular weight (MW) or MW range. Generally, polymers have a distribution of molecular weights corresponding to a collection of polymer chains within the composition. A polymer's MW is usually related to its mobility, its conformation, and other polymeric properties. Some embodiments may have an average molecular weight of at least 2,500 to engender the desired polymer properties. Other average MWs and ranges of average MWs are at least 5,000, at least 25,000, at least 100,000, at least 500,000, between 1,000 and 10,000,000, and between 2500 and 1,000,000. A person of ordinary skill in these arts will appreciate that all MW values and ranges within these explicit limits and ranges are contemplated.

Some polymers are predominantly hydrophilic. Such polymers, when wetted with water, have a slippery feel to them that can be characterized as lubricious. Lubricity is a quality that is useful in some devices, and in some medical device surfaces. A lubricious surface, for example, lends itself to ease of implantation because the surface can contact tissue in a patient with a minimum of friction.

Polymers for medical implants are preferably biocompatible with the patient that receives them. Ordinary artisans recognize the quality of biocompatibility appropriate for a particular situation. For example, the presence of toxic leachables in an implant makes materials non biocompatible in most situations. Further, a property of little or essentially no immunogenicity is recognized as being appropriate for some applications.

The Examples provide various embodiments of polymers described herein. A person of skill in these arts, after reading the Examples, will be able to adapt and apply the methods taught in the examples to practice the various embodiments of making and using copolymers described herein. Example 1 describes preparation of copolymer with monomeric units of predetermined difference in Tg, specifically, 2-Hydroxyethyl methacrylate-co-butyl acrylate-co-butyl methacrylate. Butyl acrylate forms a homopolymer of Tg −54° C., 2-Hydroxyethyl methacrylate forms a homopolymer of Tg 57° C. and butyl methacrylate forms a homopolymer of Tg 20° C.; the reactive monomers were mixed at a weight ratio of 10:11:29, respectively. Example 2 shows an alternative embodiment using the same monomeric units at different weight ratios. Examples 3-6 present other alternative embodiments, wherein copolymers have monomeric units wit certain Tg differences.

Example 6, which describes making of heparin methacrylate-co-2-hydroxyethyl methacrylate-co-butyl acrylate-co-butyl methacrylate, shows how a chemically bound anti-coagulant may be incorporated into a copolymer as one of the monomeric subunits. Heparin was decorated with a reactive functional unit that was polymerizable with reactive monomers. The heparin thus incorporated is highly stable. Other anticoagulants may be incorporated in a similar fashion. Such anticoagulants include, e.g. warfarin, hirudin, dextran sulphate, hyaluronic acid, and derivatives thereof.

Example 9 shows a preparation of polymers (e.g., copolymers) with reactive functional groups for subsequently forming covalent bonds. In Example 9, a copolymer was decorated with a reactive monomer. The reactive monomer is available for subsequent polymerization and crosslinking with other polymers. The particular example used was poly(hydroxyethyl methacrylate-co-butylacrylate-co-butylmethacrylate-methacrylate. Other Examples show this copolymer in use. Example 18 describes a copolymer having reactive functional groups that are able to react with nucleophiles to form a covalent bond. The copolymer has isocyanate groups that may subsequently form crosslinks with other polymers having suitable reactive functional groups. Example 19 describes a copolymer having reactive functional groups that are able to react with electrophiles to form a covalent bond. Example 19 further describes how copolymers with reactive electrophiles may be reacted with polymers having reactive nucleophiles to form covalent bonds between them and thereby crosslink the polymers.

Formation of Layer(s)

Polymers, e.g., copolymers, taught herein may be used to form a coating. Polymeric coatings are formed on an object. In contrast, other polymeric constructs, e.g., sheaths, sleeves, membranes, and molded objects, can be manufactured separately from a particular device. Consequently, coatings are distinct from other types of polymeric construct. For example, a sleeve, sheath, or membrane requires a certain minimum of mechanical robustness so as to maintain its identity before being associated with an object. Further, a process of coating creates an intimacy of contact between the coating and the device that is often desirable; for this reason, some processes involve coatings instead of other manufacturing procedures. Moreover, some processes of coating an object such as spraying or dipping create physical properties or processing opportunities that are not available in other processes. Further, teachings that are related to polymeric devices may not be applicable for coatings because of these differences.

It is recognized, however, that a coating can have variable characteristics. Thus a coating may be discontinuous with a surface at some points and still retain its characteristic as a coating. Coatings may also be formed of a single layer, or a plurality of layers. Coatings, and layers, can have a variable thickness, variable composition, variable chemical properties. Coatings, and layers, may cover all or a portion of a surface. Layers may, e.g., be superimposed upon other layers to create a coating.

Processes for forming a layer on an object, e.g., a medical device, may include applying a composition to a device by spraying, or by dipping the device into a composition for forming a polymeric layer. These and other methods are generally known to persons of ordinary skill in these arts. Polymers taught herein may be formed in layers upon a medical device, including a layer that covers all of a device, a layer that covers a portion of the device, and layers upon other layers. Layers that contact each other may be crosslinked to each other, e.g., by covalent crosslinks between polymers in the layers.

Some embodiments of layers are formed by preparing a composition of polymers, e.g., copolymers, and applying them to a surface. Other embodiments are layers formed by applying a composition of reactive monomers to a device or a layer and initiating polymerization to form a layer from the reactive monomers. Similarly, polymers may be applied to a device or layer and reacted there to form a layer.

Layers may also be crosslinked together. One method is to apply a first layer that has a first set of reactive functional groups, and to apply a second layer that has reactive functional groups that has a second set of reactive functional groups that form covalent crosslinks with the first set of functional groups. The first layer and second layers may be applied in any order, e.g., starting with the first, then the second, or vice versa. Additional layers may be similarly formed and used.

Layers may be made from a single type of polymer, a plurality of polymers, a single type of reactive monomer, a plurality of reactive monomer types, or a combination thereof. For example, a single type of copolymer could be used, or a plurality of copolymers, each prepared separately, could be used. Or a single reactive monomer could be mixed with reactable or unreactable polymers.

Some layers are useful for providing a base layer that contacts a device and serves to anchor subsequently applied layers. For example, a first layer with reactive functional groups may be applied to a device, and a subsequent layer may be crosslinked to the base layer. A therapeutic agent could be associated with the base layer, the subsequently applied layer, or both. A layer that overlays a layer that has a therapeutic agent can usefully serve to slow the release of the therapeutic agent in the underlying layer. Such layers may or may not be crosslinked together. Layers may have a single type of functional group, or a plurality thereof, and may be reacted with other layers having the same, similar, or complementary reactive functional groups. For example a layer having reactive monomers may be reacted with another layer having the same or difference species of reactive monomers. A polymer in a layer may have a single type of reactive functional group, or a plurality of types.

Some layers are formed by chemically reacting other layers, e.g., using surface chemistry. For example, a layer may have reactive functional groups that are exposed to a chemical composition of polymers or non-polymers that have a functional group to react thereto. Or, for example, a layer may be exposed to reactive functional groups that are reactable thereto. For example, a layer may be exposed to a composition of light-activatable molecules that are triggered by light to react with the layer. Or a layer having nucleophilic groups may be exposed to a composition of molecules having electrophilic groups that react with the nucleophiles. For instance, Example 12 describes a layer that is reacted with a heparin azide.

Any of these layers may be associated with a therapeutic agent, and may be formed on a medical device with or without the presence of a therapeutic agent. A therapeutic agent may be associated with the components of the layer, before, during, or after its application to a device. Thus a layer and a therapeutic agent may be essentially simultaneously applied to a device. Such an application has some advantages, e.g., for ease of manufacturing. For example, a copolymer may be associated with a therapeutic agent and the copolymer-therapeutic agent association may be applied to a device. Or, for example, a therapeutic agent may be part of a composition that is applied to a surface that is subsequently activated to form new copolymers. As indicated above, certain copolymers may advantageously be combined with a therapeutic agent to achieve delivery of the agent.

Therapeutic agents may be associated with a copolymer before the copolymer is applied to a device. The copolymer may be prepared and then exposed to a solution containing a solvent for the agent. The agent and the copolymer are allowed to interact, and the agent becomes associated with the copolymer, possibly by association with domains or microcavities, as discussed above. Alternatively, a therapeutic agent may be added to a melt that is used to form the copolymer.

Or the therapeutic agent may be exposed to a copolymer at essentially the same time that the agent and the copolymer are essentially simultaneously applied to a device. The agent and the copolymer could be in the same or difference solvent, or alternatively, in the same of different non-solvents that are carrier agents. The application of one or both of the copolymer and the agent in a nonsolvent would affect the resultant layer. For example, a copolymer deposited in a solvent and an agent deposited in a nonsolvent for the copolymer could help to form reservoirs, e.g., microcavities, for entrapping the therapeutics agent. Nonsolvent and solvent are terms used somewhat broadly and include their strict meanings and also as including mixtures diluted with other substances. These terms are applied in light of a particular application, and are sometimes given meanings that indicate relatively good or relatively poor solvency.

Therapeutic agents may be associated with a layer after the layer is applied to a device. One method is to expose the layer to a mixture containing the agent. The mixture may include a relatively good solvent for both the agent and the layer so that the layer is swelled and the agent migrates therethrough. When the solvent is removed, the agent is left in the layer. Examples 15 and 16 demonstrated this method, and was shown to be effective for copolymers as taught herein.

The Examples provide various embodiments of layers taught herein. A person of skill in these arts, after reading the Examples, will be able to adapt and apply the methods taught in the Examples to practice the various embodiments of making and using layers and other embodiments taught herein. Example 8 describes application of a layer to a medical device, and uses a stent as an example. The copolymer of Example 1 was applied to a stent essentially simultaneously with a therapeutic agent using a spray process. The agent and the copolymer were both in the same organic solvent. Paclitaxel was effectively loaded using this method.

Spraying was also used in other Examples. The layer thus formed was then available for use as an implant, or as a base for the addition of subsequent layers.

Example 10 shows methods for applying polymers (e.g., copolymers) as taught herein onto medical devices. The methods may involve forming a plurality of layers, with a first layer being covalently crosslinked to another layer simultaneously with, or after, the deposition of other layers. A stainless steel coronary stent was used for illustrative purposes. In this embodiment, a first reactive polymeric layer was deposited, followed by a second reactive polymeric layer containing a therapeutic agent, and an initiator that works spontaneously was used. Both polymer layers had methacrylates as the reactive functional groups for the crosslinking of the layers to each other. This Example further showed mechanical properties suitable for use on expandable medical devices such as stents or balloons. Paclitaxel was effectively loaded and released. Example 11 is an alternative embodiment demonstrating the use of a thermal initiator.

Example 13 shows the formation of a plurality of layers on a medical device and methods of crosslinking the layers. A first layer had a first reactive monomer that was used to form covalent bonds with a composition of reactive monomers that were polymerized with the first reactive monomer to simultaneously form a second layer and crosslink the second layer to the first layer. The therapeutic agent was associated with the outermost layer, but could have been associated with the innermost layer, or both layers. The therapeutic agent was, in this case, loaded into the second layer by polymerizing the second layer in the presence of the agent. This method effectively loaded the agent, e.g., see FIG. 7. Example 14 is an alternative embodiment of this method that showed the use of another scheme for initiating polymerization, in this case, in the presence of a therapeutic agent. Example 16 is similar to Example 13, but the therapeutic agent was not introduced until after the deposition of the layers. This method effectively loaded the agent.

Example 17 shows a method for coating a medical device with a first layer being a copolymer having reactive functional group crosslinked to a second layer. The first layer anchored the second layer, which contained a therapeutic agent. The agent was applied essentially simultaneously with the second layer. Initiation of polymerization of the second layer was performed after deposition of the second layer components, by use of a thermal initiator and application of heat. Alternative initiators could be used. Initiation and essentially simultaneous polymerization of the second layer could be achieved by applying an initiator with the second layer components and initiating it at that time, e.g., by applying heat to a thermal initiator, UV to a UV initiator, or by use of a spontaneous initiator.

Example 18 demonstrates the application of a plurality of layers by using a reactive copolymer in one of the layers. In this case, the layer applied to the device had reactive functional groups capable of forming covalent bonds with nucleophiles. A composition of the reactive copolymer was sprayed onto the surface to form a first layer, and then covered with a layer of a polymer that was reacted to the first layer. The polymer was chosen to be hydrophilic and lubricous, but other polymers with suitable chemical groups for reacting with the first layer could have been chosen. One embodiment was performed without a therapeutic agent and another embodiment was performed with an agent; in this case, the agent was added after the second layer was formed. These methods were successful. Similarly, other initiation and polymerization schemes, as taught herein, could have been used.

Figure 9:
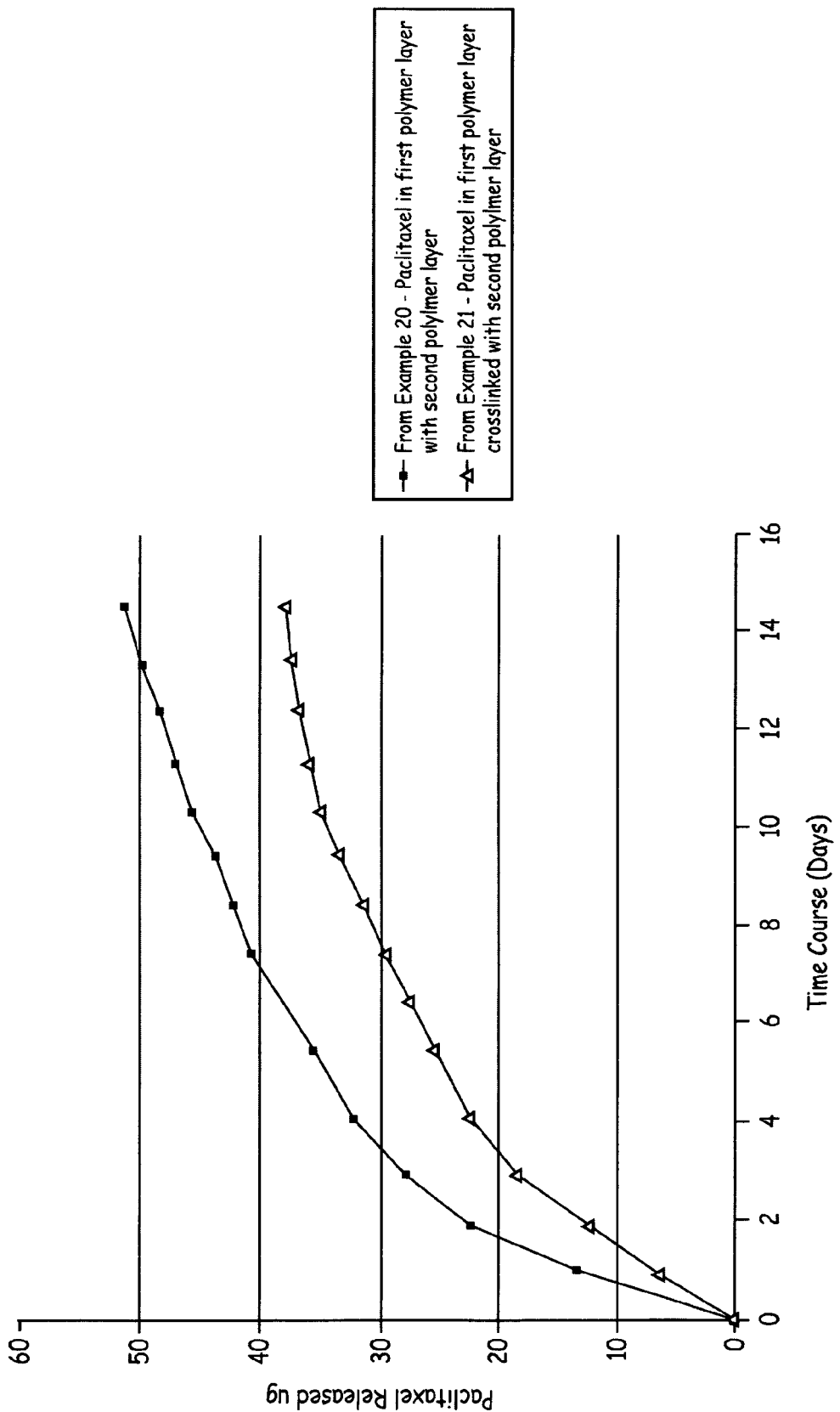
FIG. 9 shows release of a therapeutic agent from a layer, as further described in Examples 20 and 21.

Example 20 shows the formation of a plurality of layers on a device. In this embodiment, one of the layers had a therapeutic agent and the other layer did not. The layer without the agent was applied to slow release of the agent in the layer where the agent is initially disposed. The second polymer layer helped to control the diffusion of the active agent into the bulk. Example 21 was performed with similar methods, but the two layers are crosslinked together. FIG. 9 shows the release profiles for these systems.

Figure 3:
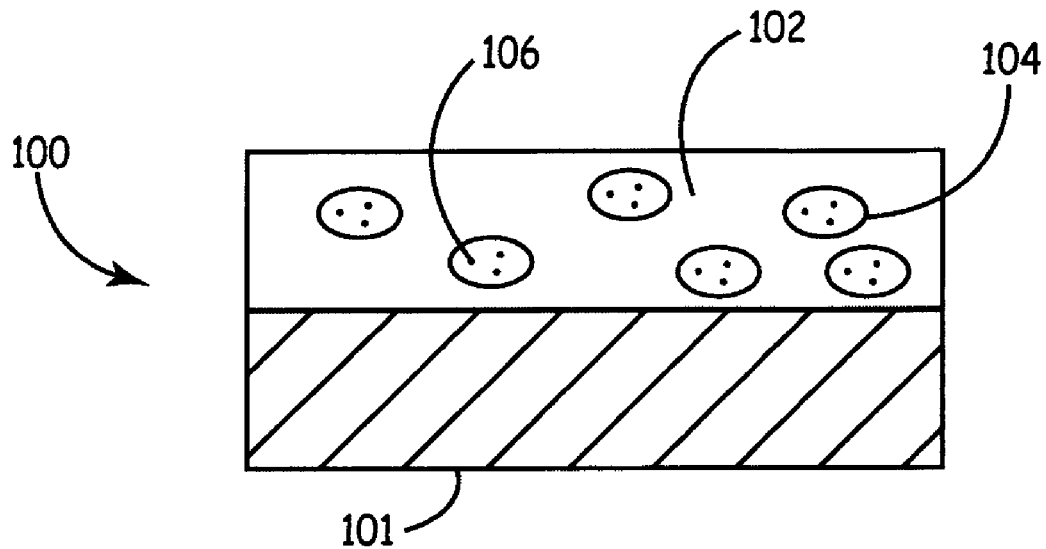
FIG. 3 is a cross sectional view of an embodiment of a coating that would be on a medical device.

Referring to FIG. 3, polymeric network coating 100 comprises a first polymeric layer 101 and reactive monomers that can react with at least first polymeric layer 101 to form a second layer 102. In some embodiments, the polymeric network 100 comprises domains or microcavities 104 located within the second layer 102 of the polymeric network 100. In some embodiments, therapeutic agents 106 are incorporated into the polymeric network 100. In one embodiment, active agents 106 are disposed in micro cavities 104 of second layer 102. In some embodiments, the size of the domains or microcavities may be about the size, e.g., the molecular weight or dimensions, of the active agents. The size and shape of the micro cavities 104 can also be varied by employing a mixture, or ratio, of different reactive monomers. In some embodiments, polymeric layer 101 comprises a polymer that is non-thrombogenic and/or anti-thrombogenic. In general, the reactive monomers should be selected so that the resulting polymeric network 100 is suitable for medical applications.

In some embodiments, active agents 106 can be water soluble, while in other embodiments active agents 106 can be soluble in organic solvents. In further embodiments, polymeric network 100 can comprise a mixture of water soluble and organic solvent soluble active agents. One of ordinary skill in the art will recognize that additional active agents are within the scope of the present disclosure.

In some embodiments, active agents 106 are disposed in the cavities 104 of the polymeric network 100. In one embodiment, active agents 106 can be disposed into the cavities 104 of the polymeric network 100 by dissolving the active agents 106 in a solvent and then coating the polymeric network 100 with the active agent/solvent mixture. Once the solvent evaporates, the active agents 106 can be disposed in the cavities 104 of polymeric network 100. Alternatively or additionally, the active agents 106 may be disposed into the cavities 104 of polymeric network 100 by mixing the active agents 106 with the reactive monomers so that the active agents 106 become disposed in the second layer 102 of polymeric network 100 as the second layer 102 is formed.

In some embodiments, active agents 106 can be released from the polymeric network 100 through micro cavities 104 to contact a site within a patient. In general, the release profile for a particular active agent can be influenced, or varied, by the size and quantity of active agents 106 relative to the size, composition and shape of micro cavities 104 of polymeric network 100. As described above, micro cavity size and shape can be influenced, or varied, by the particular selection of reactive monomers and the relative ratios of the different monomers used to form the polymeric network 100.

Figure 4:
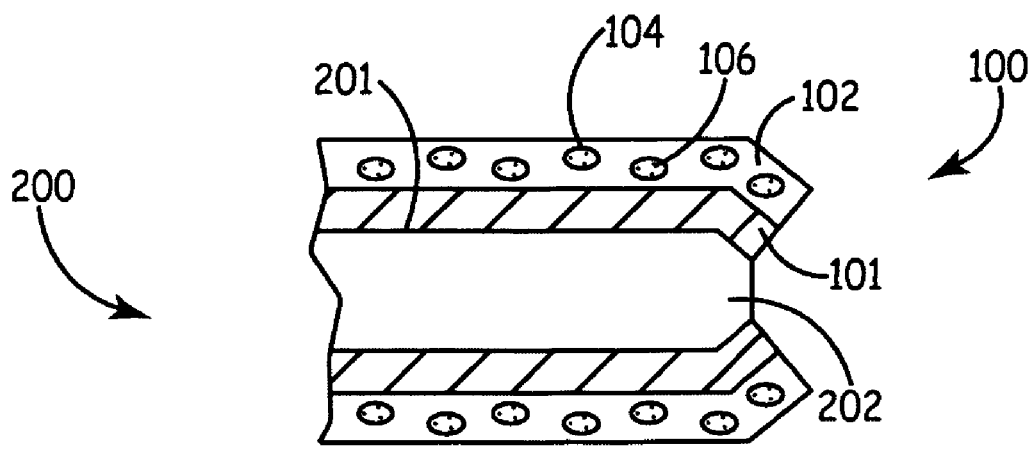
FIG. 4 is a cross sectional view of an alternative embodiment of a coating on a medical device.

As shown in FIG. 4, in some embodiments, the polymeric network 100 is coated, or formed, onto the outside surface 201 of a medical device 202. In some embodiments, the polymeric network 100 comprises micro cavities 104 in which active agents 106 are disposed. The medical device can be any medical device in which it would be beneficial to have active agents 106 releasing out of medical device during use. Examples of suitable medical devices include catheters, guide wires, vascular grafts, stents, stent grafts and the like.

In some embodiments, to form coated medical device 200, first polymeric layer 101 is applied to outside surface 201 of medical device 202. As noted above, first polymeric layer 101 should be selected so that first polymeric layer 101 adheres to outside surface 201 of medical device 202. First polymeric layer 101 can be contacted with a reactive monomer composition. The reactive monomer composition can comprise reactive monomers, and optionally polymerization initiators, polymerization catalysts and active agents 106. The reactive monomer composition can react with first polymer layer 101 to form second layer 102 of polymeric network 100 on medical device 202. In some embodiments, active agents 106 can be introduced into polymeric network 100 as polymeric network 100 is formed by mixing active agents 106 with the reactive monomer composition.

In other embodiments, polymeric network 100 can be formed and active agents 106 can be disposed into micro cavities 106 of polymeric network 100 by coating polymeric network 100 with a solvent/active agents mixture. Once the solvent has evaporated, active agents 106 can be disposed in micro cavities 104 of polymeric network 100. In embodiments where active agents 106 are introduced into the cavities 104 of polymeric network 100 through a solvent, any solvent that can deliver the active agents 106 and does not degrade or react with active agents 106 can potentially be used. In general, the choice of a particular solvent will be determined by specific active agents 106 being employed. Suitable solvents include, for example, water, alcohols, ethers, acetone, methyl ethyl ketone, and combinations thereof.

Additional embodiments are the introduction of a copolymer, layer, coating, or device as taught herein into a patient, mammal, human, animal, or in vitro system. Embodiments having a therapeutic agent may release the agent to accomplish a therapy for treatment of a medical condition. Some embodiments herein refer to layers associated with a medical device. Alternatively, the layers may be associated with a surface of a medical device, or a portion thereof. Further, a medical implant is a type of device that is implanted into a patient or placed upon a patient. A pacemaker and a catheter are implants, as would be a nicotine patch.

Medical devices include, for example any device that is implantable, used topically or comes in contact with living tissue. The devices could be made from plastic, such as catheters; from metals, such as guide-wires, stents, embolising coils; from polymeric fabric, such as vascular grafts, stent grafts; other devices include heart valves, implantable cardiovascular defibrillators, pacemakers, surgical patches, patches, wound closure, micro-spheres, biosensors, sensors (implantable, ex-vivo and analysers) ocular implants and contact lenses; medical devices that are made from ceramic, glass; tissue engineering scaffolds. Medical devices are also discussed in, e.g., U. S. Pat. Nos./patent application Ser. Nos. 5,464,650; 5,900,246; 6,214,901; 6,517,858; US 2002/0002353; and in patent applications WO 01/87342 A2; WO 03/024500.

The application of a coating to a medical device may be adapted to the particular circumstances for that device. For example, with regards to thickness, the particular application may indicate what is suitable. A stent, for example, must be threaded through a tortuous system of blood vessel to reach its pint of application in a patient. So a coating on the stent should have suitable physical properties and thickness. The thickness of the polymeric layer is of a range that a therapeutic dose is delivered without impeding the effects of the drug and the performance of the medical device, for example a stent may have a polymeric layer in the range of, e.g., about 2 µm to about 150 µm, or between about 1 and about 300 µm. Other ranges for other medical devices may vary widely, but some ranges are less than 3 mm, less than 1 mm, less than 0.1 mm, less than 0.01 mm, 1-100 µm, 10-1000, µm, 1-10,000 µm, and 10-500 µm; persons of ordinary skill in these arts will realize that all values and ranges within these explicit ranges are contemplated, and that other ranges may be suited as depending upon the device and/or application.

Some devices and applications require an expandable or a flexible layer. As set forth in the Examples, embodiments herein are provided that provide for flexibility and/or for expandability. With respect to a stent, most designs of stents require a step of expansion upon deployment in a patient. A layer that is expandable to accommodate the stent deployment is advantageous. With respect to a medical balloon, its use in the patient requires a step of expansion; accordingly, a coating on such a balloon may advantageously be made so as to accommodate that expansion.

Other Aspects of Material Formation

Polymers, e.g., copolymers, as described herein may also be used to form materials that are not layers or are not coatings, and embodiments set forth herein as layers may be applied or adapted as needed to make other materials. For example, a copolymer as taught herein may be used in a process to make a sheet, membrane, sheath, plug, implant, or a medical device. Many polymer processes are known in these arts for making such objects, e.g., molding, extrusion, and casting. Moreover, delivery devices for a therapeutic agent may be formed using a polymer as described herein, e.g., a pill, tablet, suppository.

Such constructs may be associated with a medical device to provide desired mechanical properties, e.g., lubricity, stiffness, flexibility, or expandability to provide a release of a therapeutic agent.

Stents are a medical devices that provide a scaffolding to physically hold open a tissue by deployment in a tissue; they are have a first position that is collapsed for introduction into a patient and a second position during deployment. The second position is expanded relative to the first position. Embodiments herein may be used with a stent or with a medical device that is not a stent. An embodiment herein is a coating, composition, polymer (e.g., copolymer) as taught herein that is associated with at least a portion of a medical device, wherein that device does not physically hold open a tissue by deployment in the tissue. Another embodiment is a coating, composition, polymer (e.g., copolymer) as taught herein that is associated with at least a portion of a medical device, wherein that device does not allow passage of a fluid therethrough, e.g., a pacemaker or a pacemaker lead.

An embodiment herein is a medical device, coating, or a composition comprising a copolymer as taught herein that is associated with at least a portion of an expandable portion of a medical device. Another embodiment herein is a coating, composition, polymer (e.g., copolymer) as taught herein that is associated with at least a portion of a medical device that is not expanded during use or deployment of the device.

Therapeutic Agents

Materials set forth herein may be associated with therapeutic agents, including drugs, imaging agents, diagnostic agents, prophylactic agents, hemostatic agents, tissue engineering agents, nitric oxide releasing agents, gene therapy agents, agents for enhancing wound healing, and bioactive agents. A therapeutic agent may be mixed with a polymer precursor that is in solution or disposed in a solvent, and the polymer may be formed. Alternatively, the therapeutic agent may be introduced after the polymer is formed or at an intermediate point in the polymer formation process. Certain embodiments include polymers that are made in a first solvent and exposed to a second solvent that contains the therapeutic agent so as to load the therapeutic agent into the polymer. The term therapeutic agent is used to include, for example, therapeutic and/or diagnostic agents, and/or agents that are to be released from a coating.

Therapeutic agents include, for example, vasoactive agents, neuroactive agents, hormones, growth factors, cytokines, anaesthetics, steroids, anticoagulants, anti-inflammatories, immunomodulating agents, cytotoxic agents, prophylactic agents, antibiotics, antivirals, antigens, and antibodies. Other therapeutic agents that can be provided in or on a coating material in accordance with the present invention include, but are not limited to, anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, a polylysine-containing compound, heparin, antithrombin compounds, platelet receptor antagonists, antithrombin, anti-platelet receptor antibodies, aspirin, prostaglandin inhibitors, platelet inhibitors and tick antiplatelet peptides; vascular cell growth promoters such as growth factor inhibitors, growth factor receptor antagonists, transcriptional activators, and translational promoters; vascular cell growth inhibitors such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vasoactive mechanisms. Other examples of therapeutic agents include a radiopharmaceutical, an analgesic drug, an anesthetic agent, an anorectic agent, an anti-anemia agent, an anti-asthma agent, an anti-diabetic agent, an antihistamine, an anti-inflammatory drug, an antibiotic drug, an antimuscarinic drug, an antineoplastic drug, an antiviral drug, a cardiovascular drug, a central nervous system stimulant, a central nervous system depressant, an anti-depressant, an anti-epileptic, an anxyolitic agent, a hypnotic agent, a sedative, an anti-psychotic drug, a beta blocker, a hemostatic agent, a hormone, a vasodilator, a vasoconstrictor, and a vitamin. Other therapeutic agents may be used, e.g., as set forth in U.S. patent application Nos. U.S. 6,214,901; 6,673,385; and 2002/0002353.

In some embodiments, a therapeutic agent is covalently incorporated into a layer. Example 10, for instance, shows a heparin azide that is attached to a layer. Heparin is an anticoagulant with favorable biomaterial properties. Alternatively, heparin macromers may be used as monomeric units, as polymers, or to form polymers as described herein. Heparin macromers are described in commonly owned and assigned U.S. patent applications Ser. Nos. 10/179,453, filed Jun. 26, 2002, and 10/750,706, filed Jan. 5, 2004, which are hereby incorporated by reference herein. Other anticoagulants that may be analogously used include, e.g., warfarin, hirudin, dextran sulphate, hyaluronic acid, and derivatives thereof. Other therapeutic agents may be used in conjunction with such molecules.

Other therapeutic agents may be used in conjunction with such molecules. Other examples of anti-platelets, anti-fibrin, anti-thrombin, anti-coagulants include, sodium heparin, low molecular weight heparins, heparinoids, argatroban, forskolin, vapiprost, protacyclin and protacyclin analogues, D-phe-pro-arg-chloromethyketone (synthetic anti-thrombin), other synthetic anti-thrombin, synthetic thrombin inhibitors, dipyridamole, glycoprotein IIb/IIIa platelet receptor antagonist antibody, recombinant hirudin, and thrombin inhibitors such as Anigiomax™. Other examples of anti-platelets, anti-fibrin, anti-thrombin, anti-coagulants include, sodium heparin, low molecular weight heparins, heparinoids, argatroban, forskolin,vapiprost, protacyclin and protacyclin analogues, D-phe-pro-arg-chloromethyketone (synthetic anti-thrombin), other synthetic anti-thrombin, synthetic thrombin inhibitors, dipyridamole, glycoprotein IIb/IIIa platelet receptor antagonist antibody, recombinant hirudin, and thrombin inhibitors such as Anigiomax™. Moreover, heparin, warfarin, hirudin, dextran, dextran sulphate, hyaluronic acid, derivatives thereof, and other anticoagulants may be used a releasable therapeutic agents. Other examples of anti-platelets, anti-fibrin, anti-thrombin, anti-coagulants include, sodium heparin, low molecular weight heparins, heparinoids, argatroban, forskolin, vapiprost, protacyclin and protacyclin analogues, D-phe-pro-arg-chloromethyketone (synthetic anti-thrombin), other synthetic anti-thrombin, synthetic thrombin inhibitors, dipyridamole, glycoprotein IIb/IIIa platelet receptor antagonist antibody, recombinant hirudin, and thrombin inhibitors such as Anigiomax™.

Therapeutic agents include, for example, those as disclosed in U.S. Pat. No. 6,214,901 to Chudzik et al., titled "Bioactive Agent Release Coating". Additional embodiments of therapeutic agents, as well as polymeric coating methods, reactive monomers, solvents, and the like, are set forth in U.S. Pat. Nos. 5,464,650; 5,782,908; 5,900,246; 5,980,972; 6,231, 600; 6,251,136; 6,387,379; 6,503,556; and 6,517,858. The patents and patent applications EPO950386, WO 01/01890, WO 01/87342, U.S. 2002/0002353, and U.S. patent applications Ser. Nos. 10/179,453, filed Jun. 26, 2002, and 10/750, 706, filed Jan. 5, 2004, which are hereby incorporated by reference herein.

EXAMPLES

The following materials were purchased from Sigma-Aldrich Company: 2-Hydroxyethylmethacrylate, butyl acrylate, butyl methacrylate, benzoyl peroxide (40% wt. blend in dibutyl phthalate), 2-propanol, petroleum ether (b.p. 100-120° C.), N,N-dimethyl acetamide, lauryl methacrylate, methoxy polyethylene glycol mono methacrylate (M.W. 550), dimethyl sulphoxide, tetrahydrofuran, isocyanatoethyl methacrylate, ethylene glycol dimethacrylate, benzoin methyl ether, poly(vinylchloride-co-vinyl acetate-co-vinyl alcohol), dibutyl tin dilaurate, polyvinyl pyrrolidone (average M.W. 1,300,000), aminoethylmethacrylate hydrochloride. 2,2-azobis-(2-methylbutyronitrile) was purchased from Wako Chemicals. Glycero mono methacrylate was purchased from Rohm GmbH. Bis(4-t.butyl cyclohexyl)peroxydicarbonate (Perkadox 16) was purchased from Akzo Nobel.

Example 1

Preparation of Copolymer with Monomeric Units of Predetermined Difference in Tg: 2-Hydroxyethyl methacrylate-co-butyl acrylate-co-butyl methacrylate 2-Hydroxyethyl methacrylate (11 g, 0.085 moles), butyl acrylate (10 g, 0.078 moles) and butyl methacrylate (29 g, 0.2 moles) were mixed together. A 250 ml three-necked round bottom flask fitted with a reflux condenser, thermometer and a nitrogen bleed was charged with the above monomer solution and was heated to 80° C. with stirring. Polymerisation was initiated with the addition of 2,2'-azobis-(2-methylbutyronitrile)(0.8 g). The reaction was allowed to proceed for 30 minutes, and then benzoyl peroxide (1.15 g)(40% wt. blend in dibutyl phthalate) was added. The reaction proceeded for a further 60 minutes. The temperature of the reaction was kept at 100° C.+/−5° C.

Upon cooling the above viscous mixture, 2-propanol (50 ml) was added and then poured into petroleum ether (100-120° C.)(800 ml) to precipitate the polymer. The precipitated polymer was washed twice with 300 ml of petroleum ether. 2-Propanol (100 ml) was added to dissolve the polymer with heating and stirring. Polymer was concentrated to viscous slurry with evaporation of 2-propanol. Water (1000 ml) was added to re-precipitate the polymer. After a further 2 washings with water (1000 ml) the polymer was frozen and then freeze dried. Yield=70% (32 g) Mw=44,939; Mn=13,291 Daltons; Mw/Mn=3.375 (From GPC data).

Example 2

Preparation of Copolymer with Monomeric Units of Predetermined Difference in Tg: 2-Hydroxyethyl methacrylate-co-butyl acrylate-co-butyl methacrylate, Alternative Ratios and Weight Averaged Tg 2-Hydroxyethyl methacrylate (15 g, 0.1 15 moles), butyl acrylate (25 g, 0.195 moles) and butyl methacrylate (10 g, 0.07 moles) were mixed together, polymerised to form a polymer, the polymer was purified and dried, as described in Example 1. Yield=70% (32 g) Mw=118,082; Mn=12,460 Daltons; Mw/Mn=9.47 (From GPC data)

Example 3

Preparation of Copolymer with Monomeric Units of Predetermined Difference in Tg: Poly(hydroxyethyl methacrylate-co-butylacrylate)

2-Hydroxyethyl methacrylate (20 g, 0.154 moles), butyl acrylate (30 g, 0.234 moles) and N,N-dimethylacetamide (DMA)(15 ml) were mixed together. A 250 ml three-necked round bottomed flask fitted with a reflux condenser, thermometer and a nitrogen bleed was charged with the above momoner solution in DMA and was heated to 80° C. with stirring. Polymerisation was initiated with the addition of 2,2'-azobis-(2-methylbutyronitrile)(0.8 g). The reaction was allowed to proceed for 30 minutes, and then benzoyl peroxide (115 g)(40% wt. Blend in dibutyl phthalate) was added. The reaction proceeded for a further 60 minutes. The temperature of the reaction was kept at 100° C.+/−5° C.

After cooling the above viscous polymer, was poured into water (1000 ml) to precipitate the polymer. After a further 3 washings with water (1000 ml) the polymer was frozen and then freeze dried. The freeze dried polymer was then dissolved in 2-propanol (50 ml) was added and then poured into petroleum ether at 100-120° C. (800 ml) to precipitate the polymer. The precipitated polymer was washed twice with 300 ml of petroleum ether. 2-Propanol (100 ml) was added to dissolve the polymer with heating and stirring. Polymer was concentrated to viscous slurry by evaporation of 2-propanol. Water (1000 ml) was added to re-precipitate the polymer. After a further 2 washings with water (1000 ml) the polymer was frozen and then freeze dried. Yield=35 g (70%)

Example 4

Preparation of Copolymer with Monomeric Units of Predetermined Difference in Tg: Poly(hydroxyethyl methacrylate-co-lauryl methacrylate)

2-Hydroxyethyl methacrylate (20 g, 0.154 moles), lauryl methacrylate (30 g, 0.118 moles) and N,N-dimethylacetamide (DMA)(15 ml) were mixed together, polymerised to form a polymer, the polymer was purified and dried, as described in Example 3. Yield=32.5 (65%)

Example 5

Preparation of Copolymer with Monomeric Units of Predetermined Difference in Tg: Poly(polyethylene glycol mono methacrylate-co-butyl acrylate-co-butyl methacrylate)

Methoxy (polyethyleneglycol) mono-methacrylate (MW=550)(MPEG550)(5.0 g, 0.009 moles), butyl acrylate (20 g, 0.11 7 moles) and butyl methacrylate (25 g, 0.1 75 moles) were mixed together. A 250 ml three-necked round bottom flask fitted with a reflux condenser, thermometer and a nitrogen bleed was charged with the above monomer solution in DMA and was heated to 80° C. with stirring. Polymerisation conditions, purifications steps and drying procedure were performed as described in Example 3. Yield=40 g (80%)

Example 6

Preparation of Copolymer with Monomeric Units of Predetermined Difference in Tg and a Chemically Bound Anti-coagulant (Heparin): Heparin methacrylate-co-2-hydroxyethyl methacrylate-co-Butyl acrylate-co-butyl methacrylate Heparin methacrylate was synthesized according to procedures detailed in commonly owned and assigned patent application "Polysaccharide biomaterials and methods of use thereof", PCT/GB02/02940. Heparin methacrylate (1 g) was dissolved in 2-hydroxyethyl methacrylate (15 g, 0.115 moles). Butyl acrylate (25 g, 0.195 moles), butyl methacrylate (10 g, 0.07 moles) and dimethylsulphoxide (DMSO)(15 ml) were added to the heparin methacrylate/2-hydroxyethyl methacrylate solution. A 250 ml three-necked round bottom flask fitted with a reflux condenser, thermometer and a nitrogen bleed was charged with the above monomer solution in DMSO and was heated to 80° C. with stirring. Polymerization conditions, purifications steps and drying procedure were performed as described in Example 3, above. Yield=35 g (70%)

Example 7

Preparation of Copolymer with Monomeric Units of Predetermined Difference in Tg: Preparation of Poly(glycerol mono methacrylate-co-butyl acrylate-co-butyl methacrylate)

Glycerol mono-methacrylate (Rohm GmbH)(7.5 g, 0.047 moles), butyl acrylate (10 g, 0.078 moles) and butyl methacrylate (32.5 g, 0.228 moles) were mixed together, polymerized to form a polymer, the polymer was purified and dried, as described in Example 1. Yield=35 g (70%).

Example 8

Method of Coating Copolymers with Monomeric Units of Predetermined Difference in Tg Associated with Therapeutic Agent Onto Medical Device Example 8 shows methods for applying polymers (e.g., copolymers) as taught herein onto medical devices. A stainless steel coronary stent is used for illustrative purposes. The copolymer, poly(hydroxyethyl methacrylate-co-butylacrylate-co-butylmethacrylate)(1.5 g) was dissolved in tetrahydrofuran (THF)(100 ml). To a 20 ml aliquot of the polymer solution was added the active agent paclitaxel (0.06 g). A stainless steel coronary stent (18 mm) was mounted onto a rotating mandrel and air sprayed with the above solution of THF containing polymer plus paclitaxel. The coated stent was vacuum dried at 70° C. for 30 minutes.

Paclitaxel loading on the stent was measured by incubating a coated stent in acetonitrile (3 ml), vortexing (30 seconds) and then measuring the absorbance at 227 nm wavelength; drug loading was interpolated from a standard curve. Typical drug loading per stent was 120 ug+/−10%.

Figure 5:
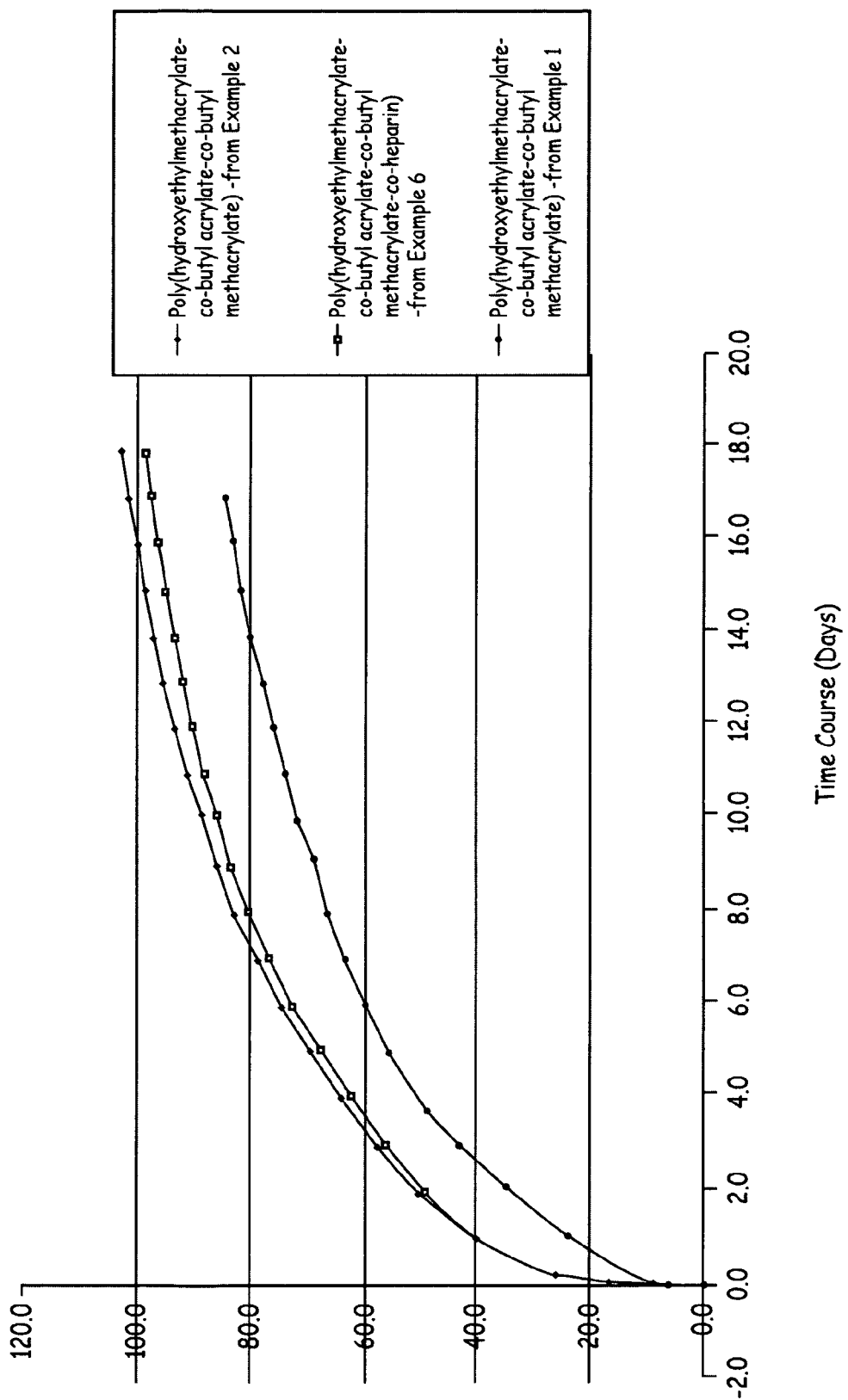
FIG. 5 shows release of a therapeutic agent from a layer, as further described in Example 8.

Paclitaxel release profiles were performed in phosphate buffer saline (PBS)(1.5 ml, pH7.4) at 37° C. Readings were taken at intervals of 1 hour, 24 hours or 48 hours. Quantification of Paclitaxel was performed on HPLC, using a Nucleosil TM 100-5CIS column (I.D.150 mm×4.6 mm) (Hichrome UK Ltd); mobile phase 50% water:50% acetonitrile; flow rate of 2.0 ml/min; column temperature 55° C.; detecting absorbance of 227 nm. FIG. 5 shows Paclitaxel release profiles at 37° C. from 3 different polymer compositions, as indicated. Persons of ordinary skill in these arts, after reading this disclosure, will be able to apply these methods to other medical devices. Polymers described or taught herein may all be applied separately, in combination, and with or without therapeutic agents using these methods.

Example 9

Preparation of Polymers (e.g., Copolymers) with Reactive Functional Groups for Forming Covalent Bonds: poly(hydroxyethyl methacrylate-co-butylacrylate-co-butylmethacrylate-methacrylate Example 9 shows methods for decorating polymers (e.g., copolymers) with a reactive functional group. In this case, the reactive functional group is a reactive monomer, specifically, a methacrylate. Polymers prepared by the methods of this Example may be used, e.g., to form layers on a medical device or on other layers.

The ter-polymer prepared in Example 2, poly(hydroxyethyl methacrylate-co-butylacrylate-co-butylmethacrylate) (20.0 g) was dissolved in tetrahydrofuran (THF)(100 ml, stabilizer free) in a 250 ml thick-walled glass bottle with cap. To this was added isocyanatoethyl methacrylate (3.58 g) and dibutyltin dilaurate (0.2 g). The cap was screwed on tight and the solution was stirred for 3 hours at 60° C. The THF was rotary evaporated off and the product dried under vacuum at 40° C. for 2 hours. Infrared spectroscopy showed the disappearance of the stretching vibration of N=C=O group at 2265 $cm^{-1}$. A urethane bond was formed between the hydroxyl group of the polymer and isocyanate group of isocyanatoethyl methacrylate.

The presence of reactive methacrylate groups on the polymer was demonstrated by dissolving 10 g of the ter-polymer in THF to which was added a peroxide initiator bis(4-tertiary butyl cyclohexyl peroxydicarbonate)(Perkadox 16)(0.5 g)(Akzo Nobel). A stainless steel rod was coated with the polymer solution, air dried and then placed in a vacuum oven at 80° C. for 30 minutes. The coated stainless steel rod was placed in the solvent 2-propanol for 5 minutes and examined using light microscopy. The polymer had swelled with 2-propanol but did not detach from the stainless steel rod. A similar sample was prepared but without heating in a vacuum, and after incubating in 2-propanol, all of the polymer dissolved away from the stainless steel rod. Persons of ordinary skill in these arts, after reading this disclosure, will be able to, apply these methods to other polymers, and will be able to incorporate reactive functional groups as set forth herein.

Example 10

Formation of a Coating on a Medical Device having Two Layers of Different Chemical Composition Covalently Crosslinked Together This Example shows methods for applying polymers (e.g., copolymers) as taught herein onto medical devices. A stainless steel coronary stent is used for illustrative purposes. In this embodiment, a first reactive polymeric layer is deposited, followed by a second reactive polymeric layer containing a therapeutic agent, and an initiator that works spontaneously was used.

The ter-polymer, poly(hydroxyethyl methacrylate-co-butylacrylate-co-butylmethacrylate) (1.5 g) prepared in Example 9 bearing methacrylate groups was dissolved in THF (100 ml). Perkadox 16 (0.5 g) was then added to the above solution. This polymer solution was air sprayed onto a stainless steel coronary stent (1 8 mm) until a thin polymer film enveloped the whole stent. The stent was air dried at 30° C. for 1 hour.

To 20 ml of the above solution, Paclitaxel (0.06 g) was added and sprayed onto the stent coated with polymer-methacrylate groups until 120 ug+/−10% of Paclitaxel was loaded. The stent was placed in a vacuum oven at 80° C. for 30 minutes to cure the coating. The methacrylates from the first layer react with the methacrylates of the second layer, containing Paclitaxel, also, the methacrylates in same layer react with each other to form the crosslinked layer structure containing the therapeutic agent. The stent was crimped onto a balloon catheter and expanded to a diameter of 3 mm and light microscopy showed no cracks or deformations. Consistent with results from Example 8, total Paclitaxel loading on stent was 120 ug+/−10%.

Example 11

Alternative Embodiment of the Formation of a Coating on a Medical Device having Two Layers of Different Chemical Composition Covalently Crosslinked Together A stainless steel coronary stent (18 mm) was coated as described in Example 10 except after spraying the second polymer layer, the coating was air dried at 30° C. for 1 hour. The initiator was initiated thermally. The coated stent was then sprayed with heparin methacrylate (0.5% w/v in 2-propanol) containing Perkadox 16 (0.2% w/v) initiator. The coated stent was then placed in a vacuum at 80° C. for 30 minutes to cross-link the coating and chemically link the heparin to the coating. The stent was then placed in saturated sodium chloride solution for 30 seconds at 40° C., to de-complex the heparin from benzalkonium chloride, and washed with water. The stent was dyed with toluidine blue and an intense purple colouration was indicative of heparin being present. The purple colouration was homogenous throughout the stent when examined by light microscopy. Stents were sprayed with the above coatings, then sprayed with benzalkonium-heparin complex (containing no methacrylate) and then placed in saturated sodium chloride solution for 30 seconds at 40° C., to de-complex the heparin from benzalkonium chloride; when dyed with toluidine blue, these showed no purple coloration. Heparin activity on stent was measured using modified ant-factor Xa chromogenic assay. Heparin activity was found to be 0.8 Units/ml equivalence. Paclitaxel loading was 120 ug+/−10%.

Figure 6:
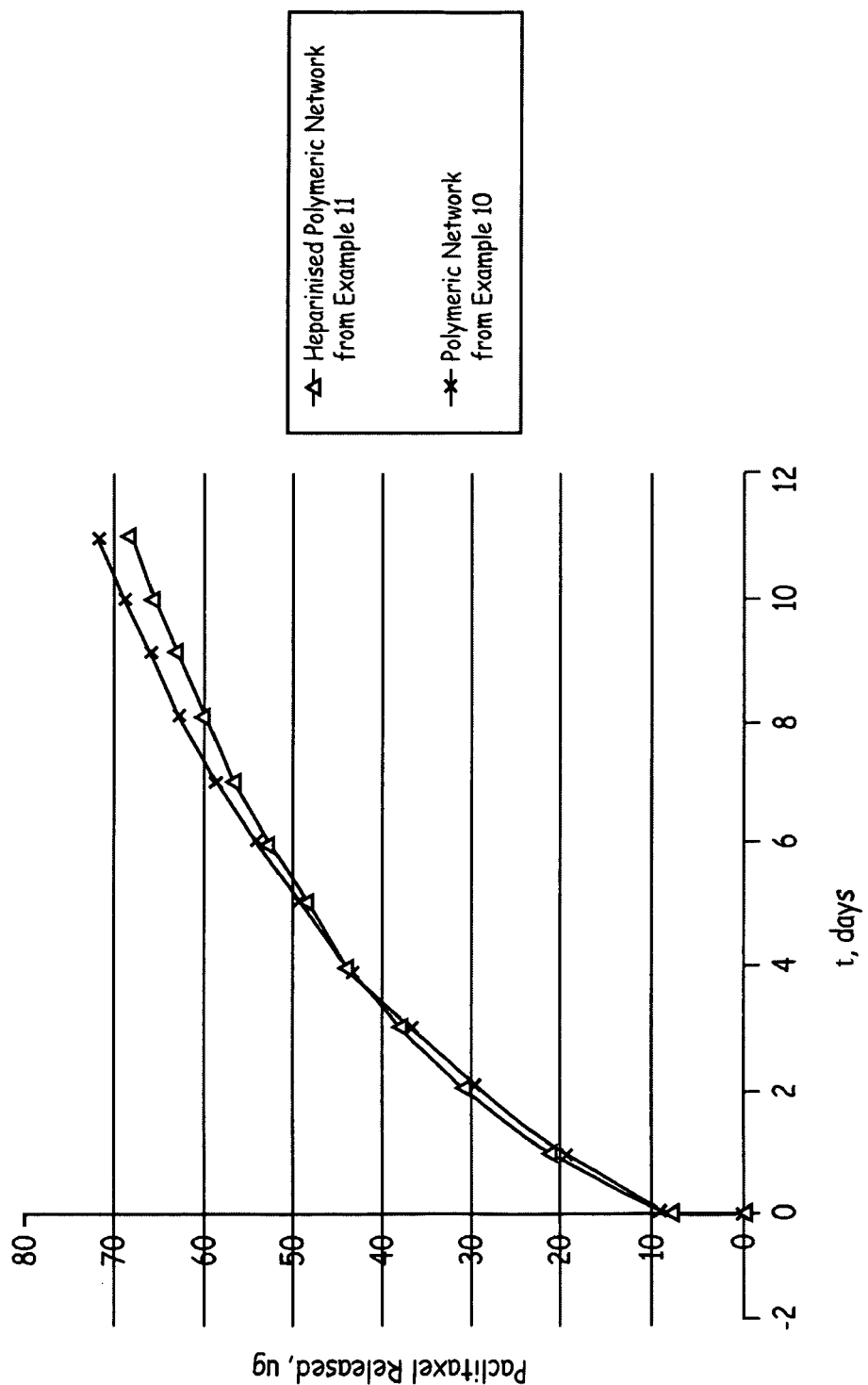
FIG. 6 shows release of a therapeutic agent from a layer, as further described in Example 11.

FIG. 6 shows paclitaxel release in phosphate buffered physiological saline at 37° C. from stents containing polymer network and polymer network with chemically bonded heparin. The results demonstrate the incorporation of heparin onto the drug delivery polymer has little effect on the delivery profile of Paclitaxel.

Example 12

Incorporation of Heparin Azide onto Drug Delivery Polymer Network

This Example demonstrates the use of photopolymerizaation to covalently crosslink two layers together. Heparin azide was synthesized according to the examples in patent application "Polysaccharide biomaterials and methods of use thereof", U.S. patent applications Ser. No. 10/179,453, filed Jun. 26, 2002, see also U.S. patent applications Ser. No. 10/750,706, filed Jan. 5, 2004. A stainless steel coronary stent (18 mm) was coated as described in Example 10, except after spraying the second polymer layer, the coating was air dried at 30° C. for 1 hour. The above coated stent was then sprayed with heparin azide (0.5% w/v in 2-propanol) and then exposed to UV light from a medium pressure mercury arc lamp for 2 minutes, to chemically link the heparin the heparin to the coating via the azide group. The stent was the placed in a vacuum oven at 80° C. for 30 minutes, so that the free reactive monomers were thereby polymerized using the thermal initiator. The stent was then placed in saturated sodium chloride solution for 30 seconds at 40° C., to de-complex the heparin from benzalkonium chloride, and then washed with water. The stent was dyed with toluidine blue and an intense purple coloration was indicative of heparin being present. The purple coloration was homogenous throughout the stent when examined by light microscopy. Heparin activity on the stent was measured using modified ant-factor Xa chromogenic assay. Heparin activity was found to be 0.7 Units/ml equivalence. Paclitaxel loading was 120 ug+/−10%. Paclitaxel release profile from the stent was very similar to the profile from Example 11.

Example 13

Coating of a Medical Device with a First Layer having a Reactive Functional Group that is Crosslinked to Functional Groups on a Second Layer that is Polymerized on the First Layer This Example shows the formation of a plurality of layers on a medical device and methods of crosslinking the layers. The therapeutic agents is associated with the outermost layer. The copolymer as prepared in Example 9, poly(hydroxyethyl methacrylate-co-butylacrylate-co-butylmethacrylate) (1.5 g) was dissolved in tetrahydrofuran (THF)(100 ml), and Perkadox 16 (0.5 g) was dissolved in the above solution. This solution was air sprayed onto a stainless steel coronary stent (18) until a thin polymer film was enveloped the whole stent. The stent was air dried at 30° C. for 1 hour.

Figure 7:
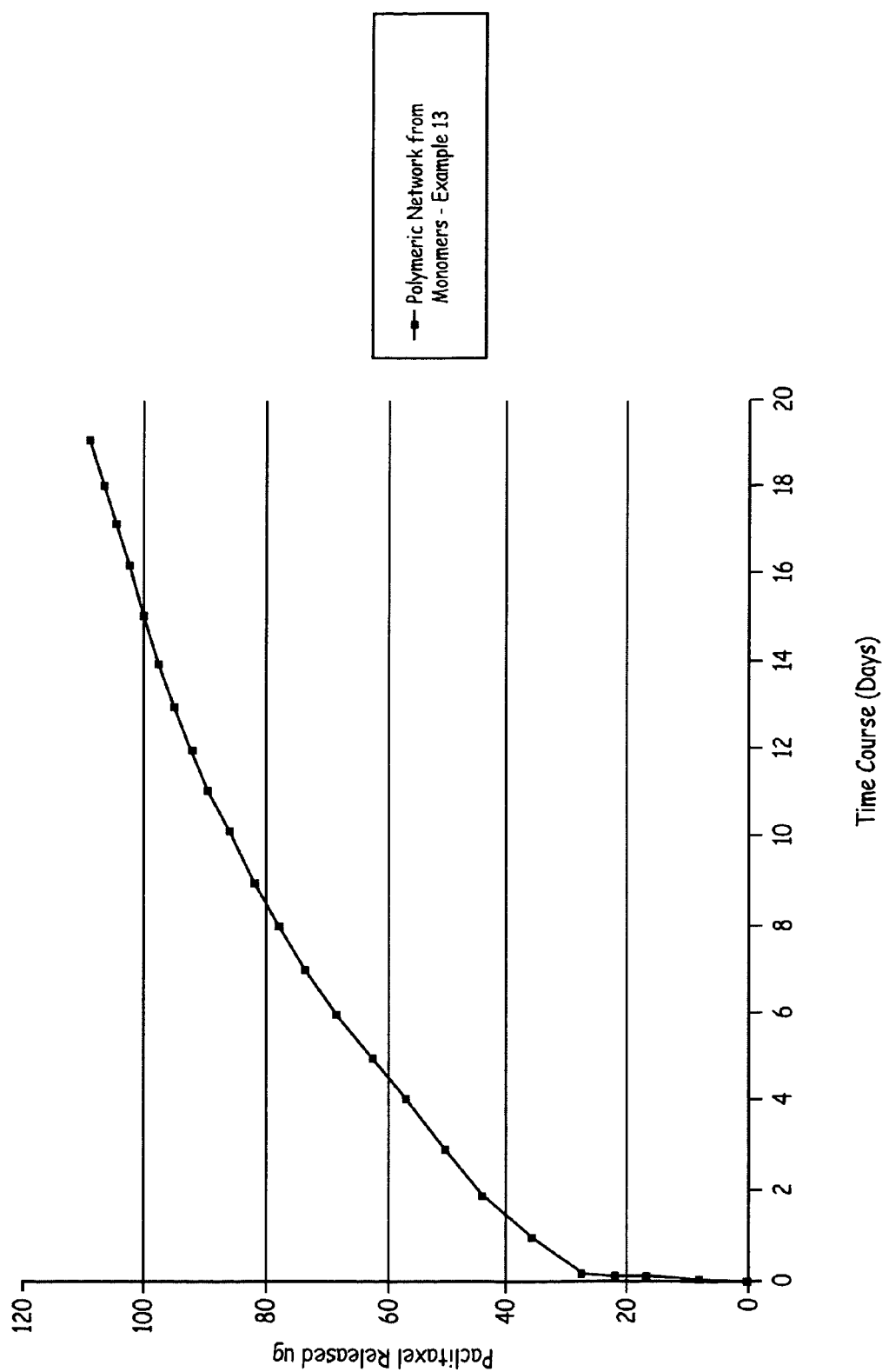
FIG. 7 shows release of a therapeutic agent from a layer, as further described in Example 13.

To THF (20 ml) was added Paclitaxel (0.06 g), Methoxy (polyethylene glycol) mono-methacrylate (MW=2000)(0.25 g), lauryl methacrylate (0.5 g), butyl methacrylate (4.0 g), ethylene glycol dimethacrylate (0.02 g) and Perkadox 16 (0.10 g). The stent was air sprayed with the above monomer solution until a Paclitaxel loading of 120 ug+/−10% was achieved. The coating was cured in an oven at 80° C. with an atmosphere of nitrogen for 1 hour. FIG. 7 shows Paclitaxel release from the stent in phosphate buffered physiological saline at 37° C., where the reactive monomers have been linked together to form a cross-linked polymer network.

Example 14

Alternative Embodiment of a Coating of a Medical Device with a First Layer having a Reactive Functional Group that is Crosslinked to Functional Groups on a Second Layer that is Polymerized on the First Layer In this Example, the monomers containing the active agent (Paclitaxel) were cross-linked and cured into a polymeric network by the use of UV light. As in Example 13, all the conditions were the same except a UV initiator was used, benzoin methyl ether, rather than Perkadox. After spraying the stent with monomers containing Paclitaxel and benzoin methyl ether on the rotating mandrel, the stent was exposed to UV light from a medium pressure mercury arc lamp in an atmosphere of nitrogen for a period of 10 minutes. The stent was examined using light microscopy. The monomers had cured to form a cross-linked network film containing the active agent, Paclitaxel.

Example 15

Loading of Layer(s) with a Therapeutic Agent

This Example shows a method for loading a therapeutic agent into a coating or certain layer(s). In this methods, the layers were deposited without the therapeutic agent, and were loaded after the layers were secured to the device. Introduction of a therapeutic agent (Paclitaxel) into the layers was performed by swelling the cross-linked layers with a solvent plus the agent, Paclitaxel. The ter-polymer as prepared in Example 9, poly(hydroxyethyl methacrylate-co-butylacrylate-co-butylmethacrylate)(1.5 g) was dissolved in tetrahydrofuran (THF)(100 ml), Perkadox 16 (0.5 g) was dissolved in the above solution. The polymer solution was air sprayed onto a stainless steel coronary stent (18) until a thin polymer film was enveloped the whole stent. The stent was air dried at 80° C. for 1 hour. The stent was placed in 20 ml 80/20 solution of 2-propanol/THF containing Paclitaxel (0.2 g) for 2 minutes. The stent was removed and air dried at 60° C. for 30 minutes. Paclitaxel loading was found to be 80 ug+/−10%. Therefore the cross-linked coating swelled in the above solution, allowing absorption of Paclitaxel into the polymer network and trapping it when air dried at 60° C.

Example 16

Alternative Embodiment of Loading of Layer(s) with a Therapeutic Agent

This Example shows another method of introducing an agent into a coating or layer(s) after they are formed. The methods described in Example 13 were followed, except the composition of reactive monomers did not contain Paclitaxel. The coating was cured at 80° C. in an oven in an atmosphere of nitrogen for 1 hour. The stent was placed in 20 ml 80/20 solution of 2-propanol/THF containing Paclitaxel (0.2 g) for 2 minutes. The stent was removed and air dried at 60° C. for 30 minutes. Paclitaxel loading was found to be 130 ug+/− 10%.

Example 17

Method for Coating a Medical Device with a Coating having a Therapeutic Agent and a First Layer with a Reactive Functional Group Crosslinked to a Second Layer This Example shows a method for layering a device with a first layer that is crosslinkable to a second layer. In this case, the second layer is a copolymer having a therapeutic agent. Poly(vinyl chloride-co-vinyl acetate-co-vinyl alcohol)(20 g) was dissolved in anhydrous THF (100 ml stabiliser free) in a 250 ml thick walled glass bottle with cap. To this was added isocyanatoethyl methacrylate (4.23 g) and dibutyltin dilaurate (0.2 g). The cap was screwed on tight and the solution was stirred for 3 hours at 60° C. As in Example 9, the polymer was processed and characterised by infrared, and functionally tested for methacrylate activity, showing that the isocyanate had linked to the vinyl alcohol of the above polymer forming a urethane linkage. This polymer was then dissolved in THF to give a 2% w/v solution containing Perkadox (0.2% w/v) and sprayed onto one side of a stainless steel disc, with a diameter of 11 mm, having a similar surface area to a 18 mm coronary stent. The coated disc was then air-dried at 30° C. for 1 hour. Poly(hydroxyethyl methacrylate-co-butylacrylate-co-butylmethacrylate) (1.5 g) bearing methacrylate groups, see Example 9, was dissolved in tetrahydrofuran (THF)(100 ml), containing Perkadox 16 (0.5 g). To a 20 ml aliquot of this solution Paclitaxel (0.6 g) was added and air sprayed onto the disc until a loading of 120 ug+/−10% was achieved. The coating was cured at 80° C. in a vacuum oven. The Paclitaxel release profile was determined as previously described (not shown) and was similar to that obtained in FIG. 6.

Example 18

Alternative Method for Coating a Medical Device with a Coating having a Therapeutic Agent and a First Layer with a Reactive Functional Group Crosslinked to a Second Layer This Example shows another method for layering a device with a first layer that is crosslinkable to a second layer. A reactive copolymer having reactive functional groups is prepared and used for the first layer. In this Example, the reactive copolymer bears isocyanate groups.

Preparation of poly(isocyanatoethyl methacrylate-co-butyl acrylate-co-butyl methacrylate In this embodiment, the method involves preparation of poly(isocyanatoethyl methacrylate-co-butyl acrylate-co-butyl methacrylate). Isocyantoethyl methacrylate (20 g, 0.129 moles), butyl acrylate (20 g, 0.156 moles) and butyl methacrylate (10 g, 0.07 moles) were mixed together. A 250 ml three-necked round bottom flask fitted with a reflux condenser, thermometer and a nitrogen bleed was charged with the above monomer solution and was heated to 80° C. with stirring. Polymerization was initiated with the addition of 2,2'-azobis-(2-methylbutyronitrile) (0.8 g). The reaction was allowed to proceed for 30 minutes, and then benzoyl peroxide (1.15 g)(40% wt. Blend in dibutyl phthalate) was added. The reaction proceeded for a further 60 minutes. The temperature of the reaction was kept at 100° C.+/−5° C. Upon cooling the above viscous mixture, THF (stabilizer free)(50 ml) was added and then poured into petroleum ether (100-120° C.) (500 ml) to precipitate the polymer. The precipitated polymer was washed twice with 300 ml of petroleum ether and then dried in a vacuum oven at 60° C. for 2 hours. Yield=40 g (80%). Infrared spectroscopy showed a sharp stretching vibration of N=C=O group at 2265 $cm^{-1}$.

Coating

A 1.5% w/v solution in THF of the above polymer was prepared and air sprayed onto one side of a stainless steel disc, with a diameter of 11 mm, having a similar surface area to a 18 mm coronary stent. The coated disc was then air-dried at 40° C. for 30 minutes. Polyvinylpyrrolidone (PVP)(average MW=1,300,000)(1 g) was dissolved in 2-propanol (100 ml) and sprayed onto the disc until an even coat was achieved and dried in an oven at 80° C. for 5 hours. The disc was immersed in water and become highly wettable, in addition the surface was lubricious. The lubricity did not diminish even after repeated and vigorous rubbing between thumb and forefinger. These results indicate that the outermost layer was covalently linked to the innermost layer.

Figure 8:
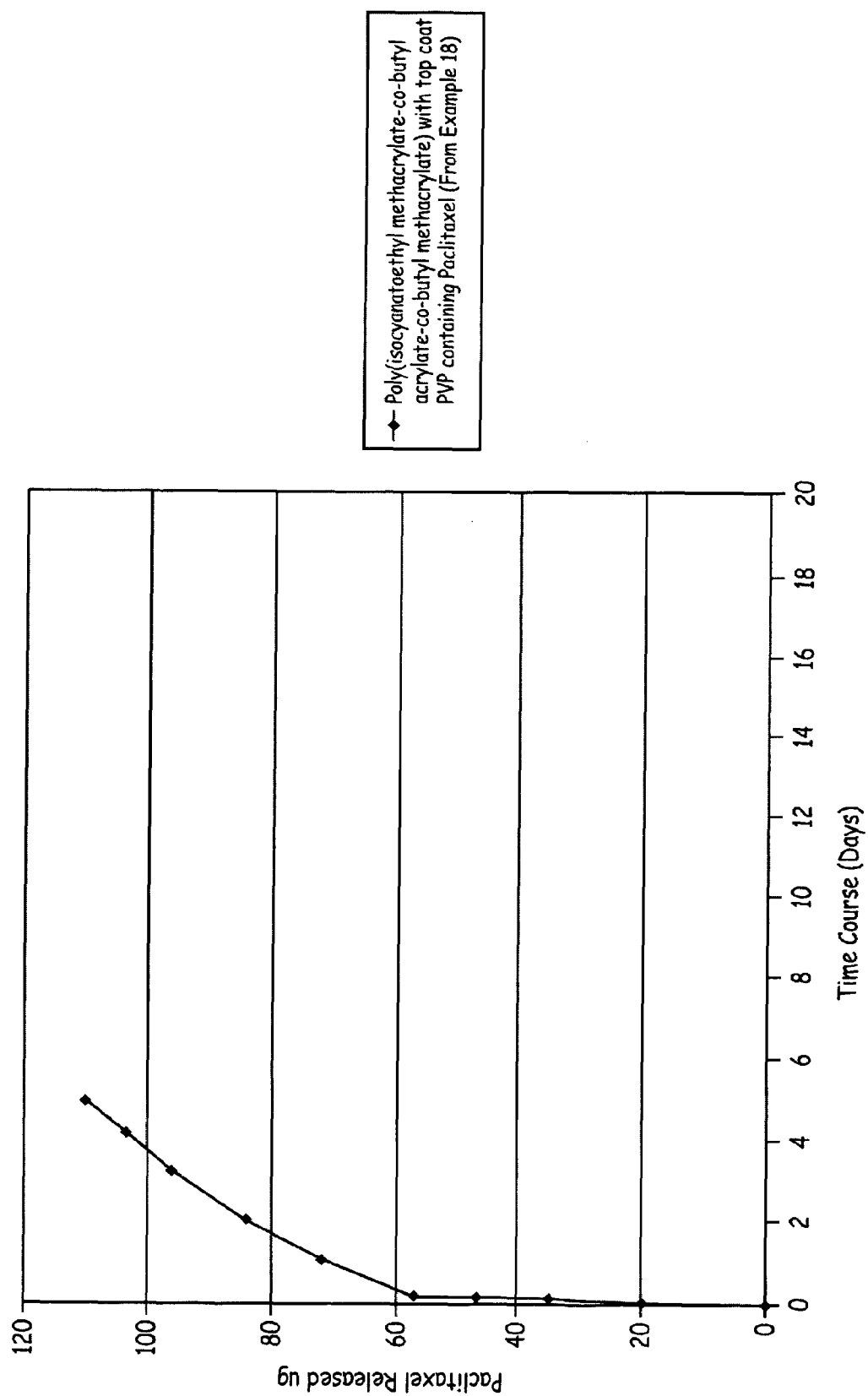
FIG. 8 shows release of a therapeutic agent from a layer, as further described in Example 18.

Another disc was also treated in a similar fashion but this time Paclitaxel was added to the PVP, (0.04 g Paclitaxel in 20 ml of 1% w/v PVP in 2-propanol), and dried in an oven at 80° C. for 5 hours. Paclitaxel loading was determined to be 120 ug+/−10% and FIG. 8 shows a fast release profile when tested in phosphate buffered physiological saline at 37° C.

Example 19

Preparation of Polymer Bearing Amine Groups as First Layer to Chemically Link a Second Polymeric Layer Containing Active Agent and thus Forming a Polymeric Network Preparation of poly(aminoethyl methacrylate hydrochloride-co-butyl acrylate-co-butyl methacrylate)

2-Aminoethyl methacrylate hydrochloride (10 g, 0.06 moles), butyl acrylate (20 g, 0.156 moles), butyl methacrylate (20 g, 0.14 moles) and N,N-dimethylacetamide (DMA)(20 ml) were mixed together. A 250 ml three-necked round bottom flask fitted with a reflux condenser, thermometer and a nitrogen bleed was charged with the above monomer solution and was heated to 80° C. with stirring. Polymerization was initiated with the addition of 2,2'-azobis-(2-methylbutyronitrile) (0.8 g). The reaction was allowed to proceed for 30 minutes, and then benzoyl peroxide (1.15 g)(40% wt. blend in dibutyl phthalate) was added. The reaction proceeded for a further 60 minutes. The temperature of the reaction was kept at 100° C.+/−5° C. After cooling the above viscous polymer, was poured into 2-propanol (50 ml) and then added to water (1000 ml) to precipitate the polymer. The polymer was washed a further 3 times (3×1000 ml water) and then frozen and freeze dried. The polymer was processed (further purification) as described in Example 3. Yield=33 g (66%)

Coating 1.5 g of the above polymer was dissolved in 2-proppanol and sprayed onto a stainless steel coronary stent (18 mm) and then dried at 80° C. for 1 hour. The coated stent was immersed in 0.1% w/v sodium hydroxide in water/methanol (75:25) solution to form the free base of aminoethyl methacrylate portion of the polymer. The stent was washed in water and dried at 60° C. for 30 minutes. The stent was air sprayed with 0.2% isocyanatoethyl methacrylate in methanol and dried in an oven at 50° C. for 10 minutes. The stent was washed with aqueous methanol (50:50) to remove unreacted isocyanatoethyl methacrylate and dried at 50° C. for 5 minutes. The second layer of the polymer containing the active agent was sprayed onto the stent as described in Example 10.

Example 20

Coating with a Plurality of Layers, with a Second Layer Applied to a First Layer to Slow Release of a Therapeutic Agent from the First Layer This Example shows the formation of a plurality of layers on a device. In this embodiment, one of the layers has a therapeutic agent and the other layer does not. The layer without the agent is applied to slow release of the agent in the layer where the agent is initially disposed. The second polymer layer helps to control the diffusion of the active agent into the bulk. From Example 8, polymer plus Paclitaxel was coated onto the stent. A second layer of polymer poly(hydroxyethyl methacrylate-co-butylacrylate-co-butyl-methacrylate)(1.5% w/v) was dissolved in tetrahydrofuran (THF) and sprayed onto the first polymer layer containing Paclitaxel and dried at 80° C. for 30 minutes.

Example 21

Alternative Embodiment of a Coating with a Plurality of Layers, with a Second Layer Applied to a First Layer to Slow Release of a Therapeutic Agent from the First Layer In this Example, the therapeutic agent is in the first polymer layer. And, the first layer and the second layer bear reactive functional groups that are able to react to crosslink link the two polymer layers. The second cross-linked layer helps to further control the release of the therapeutic agent, in this instance, Paclitaxel. All conditions are identical to Example 20 except that the polymer used for both the first and second layer is from Example 9, and Perkadox 16 (initiator) had been added and the coating cured at 80° C. in a vacuum for 30 minutes. FIG. 9 shows the release profile of Paclitaxel from these two systems in phosphate buffered physiological saline at 37° C.

The embodiments above are intended to be illustrative and not limiting. All patents, patent applications, and publications referenced herein are hereby incorporated by reference herein.

The invention claimed is:

1. A coating for a medical device for delivery of a therapeutic agent, the coating comprising a layer with a thickness between about 0.1 μm and about 1000 μm and having a composition associated with at least a portion of the device, wherein the composition comprises the therapeutic agent associated with copolymer free of covalent crosslinks that has a weight averaged molecular weight of at least about 2500, wherein the copolymer comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit.

2. The coating of claim 1 wherein at least a portion of the first monomer units are organized into a plurality of blocks consisting essentially of repeats of the first monomer unit, and at least a portion of the second monomer units are organized into a plurality of blocks consisting essentially of repeats of the second monomer unit.

3. The coating of claim 2 wherein the copolymer further comprises regions of random copolymer bonding.

4. The coating of claim 1 wherein the copolymer comprises a third monomer unit and comprises at least three blocks, wherein each block consists essentially of repeats of one type of monomer unit.

5. The coating of claim 1 wherein the copolymer comprises acrylate blocks and methacrylate blocks.

6. The coating of claim 1 wherein the therapeutic agent associates with blocks within the copolymer.

7. The coating of claim 1 wherein the second monomer unit has a glass transition temperature that is at least about 50 degrees Centigrade higher than the glass transition temperature of the first monomer unit.

8. The coating of claim 1, wherein the second monomer unit has a glass transition temperature that is at least about 70 degrees Centigrade higher than the glass transition temperature of the first monomer unit.

9. The coating of claim 1 wherein the first monomer unit comprises an acrylate and the second monomer unit compromises a methacrylate.

10. The coating of claim 1 wherein the first monomer unit and the second monomer unit selected from a member of the group consisting of acrylic acid, acrlonitrile, allyamine, acrylates, methacrylates, methylmethacrylate, alkyl acrylates, alkyl methacrylate, butadiene, carbomethylsilane, (carbonate) urethane, acrylates of polydimethyl siloxanes, methacrylates of polydimethyl siloxanes, ethylene, ethylene glycol, propylene glycol, (ether) urethane, urethane, vinyl chloride, vinyl alcohol, maleic anhydride, cellulose nitrate, carboxy methyl cellulose, dextran, dextran sulphate, propylene, esters, carbonates, ethers, butenes, maleic acid, fluoropolymer monomeric units, unsaturated polymer monomeric units, isoprene, melamine, sulphone, ureas, biological polymer monomeric units, protein, gelatin, collagen, elastin, butyl methacrylate, hydroxyethyl methacrylate, methacrylate acid, polyethylene glycol dimethacrylate, polypropylene glycol diglycidal ether, polyethylene glycol diglycidyl ether, isocyanatoethyl methacrylate, N-acryloxysuccinimide, glycidyl methacrylate, hexamethylene diisocyanate, acrolein, crotonaldehyde, glycerol monomethacrylate, heparin methacrylate, methacryloylethyl phosphorylcholine, polymethacrylatea, polyacrylate, polyester, polyether, polyethylene glycol, butyl acrylate, polyethylene glycol monomethacrylate, isobutyl methacrylate, cyclohexyl methacrylate, ethyl acrylate, 2-hydroxyethyl acrylate, 2-ethylhexyl methacrylate, ethyl methacrylate, methyl acrylate, hexadecyl methacrylate, octadecyl methacrylate, styrene, methyl styrene, vinyl sterate, vinyl toluene, and tert-butyl acrylate.

11. The coating of claim 1 wherein the copolymer father comprises a third monomer unit, wherein the third monomer unit forms a homopolymer wit a glass transition temperature that is at least about 30 degrees Centigrade higher than the glass transition temperature of a homopolymer formed by the first monomer unit.

12. The coating of claim 11 wherein the first monomer unit comprises an acrylate, the second monomer unit compromises a methacrylate, and the third monomer unit comprises a methacrylate.

13. The coating of claim 11 wherein the copolymer comprises a homopolymer of the first monomer unit covalently joined to a homopolymer of the second monomer unit.

14. The coating of claim 13 wherein a first polymer comprises a first monomer unit and a second polymer comprises at least one member of the group consisting of the first monomer unit, the second monomer unit, and both the first monomer unit and the second monomer unit.

15. The coating of claim 1 wherein the copolymer comprises at least two methacrylate monomer units.

16. The coating of claim 1 wherein the copolymer comprises a member of the group consisting of poly(hydroxyethyl methacrylate-co-butylacrylate-co-butylmethacrylate), poly(hydroxyethyl methacrylate-co-lauryl methacrylate), poly(polyethylene glycol monomethacrylate-co-butyl acrylate-co-butyl methacrylate), poly(heparin methacrylate-co-hydroxyethylmethacrylate-co-butyl acrylate-co-butyl methacrylate), poly(glycerol monomethacrylate-co-butyl acrylate-co-butyl methacrylate), poly(amino methacrylate hydrochloride-co-butyl acrylate-co-butyl methacrylate), poly(isocyanatoethyl methacrylate-co-butyl acrylate-co-butyl methacrylate) and poly (methoxy(polyethylene glycol) monomethacrylate-co-lauryl methacrylate-co-butyl methacrylate-co-ethylene glycol dimethacrylate).

17. The coating of claim 1 wherein the monomer units are polymerizable to form the copolymer after the monomer units have been associated with the medical device.

18. The coating of claim 1 wherein the medical device is a stent and the therapeutic agent is paclitaxel.

19. The coating of claim 1 wherein the copolymer is prepared and is subsequently associated with the therapeutic agent.

20. The coating of claim 1 wherein the copolymer is prepared from the monomer units from a melt of the monomers.

21. The coating of claim 1 wherein the first monomer unit and the second monomer unit are chosen so that the first monomer unit reacts to form a plurality of blocks consisting essentially of repeats of the first monomer unit and the second monomer unit reacts to form a plurality of blocks consisting essentially of repeats of the second monomer unit.

22. The coating of claim 1 further comprising a second layer that contacts at least a portion of the first layer, wherein the second layer and the first layer have a different composition.

23. The coating of claim 22 wherein the first layer is at least partially disposed between the device and the second layer.

24. The coaling of claim 22 wherein the second layer is at least partially disposed between the device and the first layer.

25. The coating of claim 22 wherein the second layer comprises a polymer that is covalently crosslinked to a polymer of the first layer.

26. The coating of claim 25 wherein the copolymer comprises reactive functional groups that are involved in forming covalent crosslinks with the second layer, and wherein the reactive functional groups are chosen from the group consisting of hydroxyl, amine, carboxylic, aldehyde, ketone, thiol, ally), acrylate, methacrylate, isocyanate, epoxide, azides, aziridines, acetals, ketals, alkynes, acyl halides, alky halides, hydroxy aldehydes and ketones, allenes, amides, bisamides, amino acids and esters, amino carbonyl compounds, mercaptans, amino mercaptans, anhydrides, azines, azo compounds, azoxy compounds, boranes, carbamates, carbodimides, carbonates, diazo compounds, isothionates, hydroxamic acid, hydroxy acids, hydroxy amines and amides, hydroxylamine, imines, lactams, nitriles, sulphonamides, sulphones, sulphonic acids, thiocyanates, and combinations thereof.

27. The coating of claim 25 wherein the second layer comprises a heparin macromer that comprises a second reactive functional group that is involved in forming the crosslinks with the first layer.

28. The coating of claim 25 wherein the polymer of the second layer comprises monomer units that comprise a heparin macromer.

29. The coating of claim 25 wherein the polymer of the second layer comprises a second functional group that forms at least one of the covalent crosslinks in response to exposure to light.

30. The coating of claim 29 wherein the second functional group comprises azide.

31. The coating of claim 22 wherein the first layer comprises the therapeutic agent and the second layer does not comprise the therapeutic agent.

32. The coating of claim 22 wherein the second layer reduces the rate of release of the therapeutic agent from the first layer.

33. The coating of claim 22 wherein the second layer is in contact with the medical device and comprises a polymer having at least one reactable monomer.

34. The coating of claim 33 wherein the at least one reactable monomer is a member of the group consisting of acrylates and methylmethacrylates.

35. The coating of claim 34 wherein the polymer in the second layer is a second copolymer that comprises monomer units of at least one member of the group consisting of vinyl chloride, vinyl acetate, and co-vinyl alcohol.

36. The coating of claim 34 wherein the polymer in the second layer comprises a hydrophillic polymer.

37. The coating of claim 36 wherein the polymer in the second layer comprises polyvinylpyrrolidone.

38. The coating of claim 22 further comprising a third layer having a composition different from the first layer and the second layer.

39. The coating of claim 1 wherein the therapeutic agent is a member of the group consisting of, vasoactive agents, neuroactive agents, hormones, growth factors, cytokines, anaesthetics, steroids, anticoagulants, anti-inflammatories, immunomodulating agents, cytotoxic agents, antibiotics, antivirals, antibodies, anti-thrombogenic agents such as heparin, heparin derivatives, urokinase, and PPack (dextrophenylalanine proline arginine chloromethylketone); anti-proliferative agents such as enoxaprin, angiopeptin, antibodies capable of blocking smooth muscle cell proliferation, hirudin, acetylsalicylic acid; anti-inflammatory agents, dexamethasone, prednisolone, corticosterone, budesonide, estrogen, sulfasalazine, and mesalamine, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants, D-Phe-Pro-Arg chloromethyl ketone, an RGD peptide-containing compound, heparin, antithrombin compounds, platelet receptor antagonists, anti-thrombin, anti-platelet receptor antibodies, aspirin, prostaglandin inhibitors, platelet inhibitors, antiplatelet peptides, vascular cell growth promoters, growth factor inhibitors, growth factor receptor antagonists, transcriptional activators, translational promoters, vascular cell growth inhibitors, growth factor receptor antagonists, transcriptional repressors, translational repressors, replication inhibitors, inhibitory antibodies, antibodies directed against growth factors, cholesterol-lowering agents, vasodilating agents, agents which interfere with endogenous vasoactive mechanisms, a radiopharmaceutical, an analgesic drug, an anesthetic agent, an anorectic agent, an anti-anemia agent, an anti-asthma agent, an anti-diabetic agent, an antihistamine, an anti-inflammatory drug, an antibiotic drug, an antimuscarinic drug, an anti-neoplastic drug, an antiviral drug, a cardiovascular drug, a central nervous system stimulator, a central nervous system depressant, an anti-depressant, an anti-epileptic, an anxyolitic agent, a hypnotic agent, a sedative, an anti-psychotic drug, a beta blocker, a hemostatic agent, a hormone, a vasodilator, a vasoconstrictor, and a vitamin.

40. The coating of claim 1 wherein the therapeutic agent comprises paclitaxel.

41. The coating of claim 1 wherein the device is selected from the group consisting of an implantable device, a device used topically on a patient, a device that contacts a living tissue, a catheter; a guide-wires, an embolizing coil; a vascular graft, a heart valve, an implantable cardiovascular defibrillator, a pacemaker, a surgical patch, a wound closure, a microsphere, a biosensors, an implantable sensor, an ex-vivo sensor, an ocular implant, a contact lens; and a tissue engineering scaffold.

42. The coating of claim 1 wherein the device comprises a stent.

43. The coating of claim 1 wherein the glass transition temperature of the first monomer unit is below about 37 degrees Centigrade and the glass transition temperature of the second monomer unit is above about 37 degrees Centigrade.

44. The coating of claim 1 wherein the copolymer is made from a combination of monomer units and has a glass transition temperature in a range of about 0 to about 60 degrees Celsius as measured using differential scanning calorimetery.

45. The coating of claim 1 wherein the copolymer is made from a combination of monomer units and has a glass transition temperature in a range of about 15 to about 40 degrees Celsius as measured using differential scanning calorimetery.

46. The coating of claim 1 wherein the copolymer is made from a combination of monomer units and has a glass transition temperature in a range of about −70 to about 70 degrees Celsius as measured using differential scanning calorimetery.

47. The coating of claim 46 wherein the combination comprises at least one monomer unit selected from the group consisting of butyl acrylate, butyl methylmethacrylate, and hydroxyethylmethacrylate.

48. The coating of claim 46 wherein the first monomer unit and the second monomer unit are selected from a member of the group consisting of acrylic acid, acrionitrile, allyamine, acrylates, methacrylates, methylmethacrylate, alkyl acrylates, alkyl methacrylate, butadiene, carbomethylsilane, (carbonate) urethane, acrylates of polydimethyl siloxanes / methacrylates of polydimethyl siloxane ethylene, ethylene glycol, propylene glycol, (ether) urethane, urethane, vinyl chloride, vinyl alcohol, maleic anhydride, cellulose nitrate, carboxy methyl cellulose, dextran, dextran sulphate, propylene, esters, carbonates, ethers, butenes, maleic acid, fluoropolymer monomeric units, unsaturated polymer monomeric units, isoprene, melamine, sulphone, ureas, biological polymer monomeric units, protein, gelatin, collagen, elastin, butyl methacrylate, hydroxyethyl methacrylate, acrylic acid, methacrylate acid, polyethylene glycol dimethacrylate, polypropylene glycol diglycidal ether, polyethylene glycol diglycidyl ether, isocyanatoethyl methacrylate, N-acryloxysuccinimide, glycidyl methacrylate, hexamethylene diisocyanate, acrolein, crotonaldehyde, glycerol monomethacrylate, heparin methacrylate, methacryloyloxyethyl, methacryloylethyl phosphorylcholine polyacrylate, polyester, polyether, polyethylene glycol, butyl acrylate, polyethylene glycol monomethacrylate, isobutyl methacrylate, cyclohexyl methacrylate, ethyl acrylate, 2-hydroxyethyl acrylate, 2-ethylhexyl methacrylate, ethyl methacrylate, methyl acrylate, hexadecyl methacrylate, octadecyl methacrylate, styrene, methyl styrene, vinyl sterate, vinyl toluene, and tert-butyl acrylate.

49. The coating of claim 46 wherein the copolymer further comprises a third monomer unit, wherein the third monomer unit forms a homopolymer with a glass transition temperature that is at least about 30 degrees Centigrade higher than the glass transition temperature of a homopolymer formed by the first monomer unit.

50. The coating of claim 46 wherein the first monomer unit comprises an acrylate, the second monomer unit compromises a methacrylate, and the third monomer unit comprises a methacrylate.

51. The coating of claim 46 wherein the copolymer comprises at least two methacrylate monomer units.

52. The coating of claim 42 wherein the coating is disposed essentially only on the solid portions of the stent.

53. The coating of claim 42 wherein the coating is disposed on both a lumen and exterior of the stent.

54. An expandable medical device associated with a material composition for delivery of a therapeutic agent, comprising: an expandable portion of an expandable stern coated with a composition comprising the therapeutic agent associated with a copolymer free of covalent crosslinks that has a weight averaged molecular weight of at least about 2500, wherein the copolymer comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit.

55. The device of claim 54 wherein at least a portion of the first monomer units are organized into a plurality of blocks consisting essentially of repeats of the first monomer unit, and at least a portion of the second monomer units are organized into a plurality of blocks consisting essentially of repeats of the second monomer unit.

56. The device of claim 55 wherein the copolymer further comprises regions of random copolymer bonding.

57. The device of claim 55 wherein the copolymer comprises acrylate blocks and methacrylate blocks.

58. The device of claim 54 wherein the copolymer comprises a third monomer unit and comprises at least three blocks, wherein each block consists essentially of repeats of one type of monomer unit.

59. The device of claim 54 wherein the therapeutic agent associates with blocks within the copolymer.

60. The device of claim 54, wherein the second monomer unit has a glass transition temperature that is at least about 70 degrees Centigrade higher than the glass transition temperature of the first monomer unit.

61. The device of claim 54 wherein the monomer units are polymerizable to form the copolymer after the monomer units have been associated with the medical device.

62. The device of claim 54 wherein the therapeutic agent is paclitaxel.

63. The device of claim 54 wherein the copolymer is prepared and is subsequently associated with the therapeutic agent.

64. The device of claim 54 wherein the copolymer is prepared from the monomer units from a melt of the monomers.

65. The device of claim 54 wherein the first monomer unit and the second monomer unit are chosen so that the first monomer unit reacts to form a plurality of blocks consisting essentially of repeats of the first monomer unit and the second monomer unit reacts to form a plurality of blocks consisting essentially of repeats of the second monomer unit.

66. The device of claim 54 further comprising a second layer that contacts at least a portion of the first layer, wherein the second layer and the first layer have a different composition.

67. The device of claim 66 wherein the second layer comprises a polymer that is covalently crosslinked to a polymer of the first layer.

68. The device of claim 67 wherein the polymer of the second layer comprises monomer units that comprise a heparin macromer.

69. The device of claim 66 wherein the polymer of the second layer comprises a second functional group that forms at least one of the covalent crosslinks in response to exposure to light.

70. The device of claim 54 wherein the copolymer glass transition temperature is between 26 and about 40 degrees Centigrade.

71. The device of claim 54 wherein the composition associated with the stent has a thickness ranging from about 0.1 µm to about 30 µm.

72. The coating of claim 1 wherein the thickness ranges from about 1 µm to about 200 µm.

73. The coating of claim 54 wherein the coating is disposed essentially only on the solid portions of the stent.

74. The coating of claim 54 wherein the coating is disposed on both a lumen and exterior of the stent.

75. A coating for a medical device for delivery of a therapeutic agent, the coating comprising a layer having a composition associated with at least a portion of the device, wherein the composition comprises the therapeutic agent associated with a copolymer that has a weight averaged molecular weight of at least about 2500 and a glass transition temperature between 26 and about 40 degrees Centigrade as measured by differential scanning calorimetery, wherein the copolymer comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of tat monomer unit, wherein the layer has a glass transition temperature between 26 and about 40 degrees Centigrade as measured by differential scanning calorimetery.

76. The coating of claim 75 wherein at least a portion of the first monomer units are organized into a plurality of blocks consisting essentially of repeats of the first monomer unit, and at least a portion of the second monomer units are organized into a plurality of blocks consisting essentially of repeats of the second monomer unit.

77. The coating of claim 75 wherein the copolymer further comprises regions of random copolymer bonding.

78. The coating of claim 75 wherein the copolymer comprises a third monomer unit and comprises at least three blocks, wherein each block consists essentially of repeats of one type of monomer unit.

79. The coating of claim 75 wherein the copolymer comprises acrylate blocks and methacrylate blocks.

80. The coating of claim 75 wherein the therapeutic agent associates with blocks within the copolymer.

81. The coating of claim 75, wherein the second monomer unit has a glass transition temperature that is at least about 70 degrees Centigrade higher than the glass transition temperature of the first monomer unit.

82. The coating of claim 75 wherein the monomer units are polymerizable to form the copolymer after the monomer units have been associated with the medical device.

83. The coating of claim 75 wherein the medical device is a stent and the therapeutic agent is paclitaxel.

84. The coating of claim 75 wherein the copolymer is prepared and is subsequently associated with the therapeutic agent.

85. The coating of claim 75 wherein the copolymer is prepared from the monomer units from a melt of the monomers.

86. The coating of claim 75 wherein the first monomer unit and the second monomer unit are chosen so that the first monomer unit reacts to form a plurality of blocks consisting essentially of repeats of the first monomer unit and the second monomer unit reacts to form a plurality of blocks consisting essentially of repeats of the second monomer unit.

87. The coating of claim 75 further comprising a second layer that contacts at least a portion of the first layer, wherein the second layer and the first layer have a different composition.

88. The coating of claim 87 wherein the second layer comprises a polymer that is covalently crosslinked to a polymer of the first layer.

89. The coating of claim 88 wherein the polymer of the second layer comprises monomer wilts that comprise a heparin macromer.

90. The coating of claim 88 wherein the polymer of the second layer comprises a second functional group that forms at least one of the covalent cross links in response to exposure to light.

91. The coating of claim 75 wherein the medical device is a stent, with the coating being applied to every expandable portion of the stent.

92. The coating of claim 75 wherein the medical device is a member of the group consisting of an implantable device, a device used topically on a patient, a device that contacts a living tissue, a catheter; a guide-wires, an embolizing coil, an implantable lead, an expandable balloon, a vascular graft, a heart valve, an implantable cardiovascular defibrillator, a pacemaker, a surgical patch, a wound closure, a microsphere, a biosensors, an implantable sensor, an ex-vivo sensor, an ocular implant, a contact lens, and a tissue engineering scaffold.

93. The coating of claim 75 having a thickness of between about 0.1 μm and about 1000 μm.

94. The coating of claim 75 having a thickness of between about 1 μm and about 200 μm.

95. The copolymer of claim 70 wherein the copolymer glass transition temperature is about 37°C.

96. The coating of claim 75 wherein the layer glass transition temperature is about 37°C.

97. A coaling for a medical device for delivery of a therapeutic agent, the coating comprising a layer having a composition associated wit at least a portion of the device, wherein the composition comprises the therapeutic agent associated with a copolymer free of covalent crosslinks that has a weight averaged molecular weight of at least about 2500, wherein the copolymer comprises a first monomer unit and a second monomer unit, wherein the second monomer unit has a glass transition temperature that is at least about 30 degrees Centigrade higher than the glass transition temperature of the first monomer unit, with a glass transition temperature of a monomer unit being defined as a glass transition temperature of a homopolymer of that monomer unit, wherein the device is selected from the group consisting of an implantable device, a device used topically on a patient, a device that contacts a living tissue, a catheter; a guide-wires, an embolizing coil, an implantable lead, an expandable balloon, a vascular graft, a heart valve, an implantable cardiovascular defibrillator, a pacemaker, a surgical patch, a wound closure, a microsphere, a biosensors, an implantable sensor, an ex-vivo sensor, an ocular implant, a contact lens, and a tissue engineering scaffold.

98. The coating of claim 97 wherein at least a portion of the first monomer units are organized into a plurality of blocks consisting essentially of repeats of the first monomer unit, and at least a portion of the second monomer units are organized into a plurality of blocks consisting essentially of repeats of the second monomer unit.

99. The coating of claim 98 wherein the copolymer further comprises regions of random copolymer bonding.

100. The coating of claim 97 wherein the copolymer comprises a third monomer unit and comprises at least three blocks, wherein each block consists essentially of repeats of one type of monomer unit.

101. The coating of claim 97 wherein the copolymer comprises acrylate blocks and methacrylate blocks.

102. The coating of claim 97 wherein the therapeutic agent associates with blocks within the copolymer.

103. The coating of claim 97, wherein the second monomer unit has a glass transition temperature that is at least about 70 degrees Centigrade higher than the glass transition temperature of the first monomer unit.

104. The coating of claim 97 wherein the monomer units are polymerizable to form the copolymer after the monomer units have been associated with the medical device.

105. The coating of claim 97 wherein the copolymer is prepared and is subsequently associated with the therapeutic agent.

106. The coating of claim 97 wherein the copolymer is prepared from the monomer units from a melt of the monomers.

107. The coating of claim 97 wherein the first monomer unit and the second monomer unit are chosen so that the first monomer unit reacts to form a plurality of blocks consisting essentially of repeats of the first monomer unit and the second monomer unit reacts to form a plurality of blocks consisting essentially of repeats of the second monomer unit.

108. The coating of claim 97 further comprising a second layer that contacts at least a portion of the first layer, wherein the second layer and the first layer have a different composition.

109. The coating of claim 108 wherein the second layer comprises a polymer that is covalently crosslinked to a polymer of the first layer.

110. The coating of claim 109 wherein the polymer of the second layer comprises monomer units that comprise a heparin macromer.

111. The coating of claim 109 wherein the polymer of the second layer comprises a second functional group that forms at least one of the covalent crosslinks in response to exposure to light.

112. The coating of claim 97 wherein the copolymer has a glass transition temperature between 26 and about 40 degrees Centigrade.

113. The coating of claim 97 having a thickness of between about 0.1 μm and about 1000 μm.

* * * * *